United States Patent
Gall

[11] 4,010,177
[45] * Mar. 1, 1977

[54] [3-SUBSTITUTED-5-[(DI-METHYLAMINO)-METHYL]-4H-1,2,4-TRIAZOL-4-YL]BENZOPHENONES AND PROCESS

[75] Inventor: Martin Gall, Kalamazoo, Mich.

[73] Assignee: The Upjohn Company, Kalamazoo, Mich.

[ * ] Notice: The portion of the term of this patent subsequent to Sept. 23, 1992, has been disclaimed.

[22] Filed: June 6, 1975

[21] Appl. No.: 584,616

[52] U.S. Cl. .................. 260/308 R; 260/247.1 M; 260/247.1 E; 260/247.2 R; 260/293.69; 424/248.56; 424/267; 424/269
[51] Int. Cl.² ............. C07D 249/08; C07D 401/06; C07D 403/06; C07D 413/06
[58] Field of Search .............. 260/308 R, 247.1 M, 260/247.5 E, 247.2 R, 293.69, 247.1 E, 247.1 CA

[56] References Cited
UNITED STATES PATENTS

| | | | |
|---|---|---|---|
| 3,856,792 | 12/1974 | Hester | 260/308 R |
| 3,879,413 | 4/1975 | Hester | 260/308 R |
| 3,907,821 | 9/1975 | Gall | 260/308 R |

Primary Examiner—Alton D. Rollins
Attorney, Agent, or Firm—Hans L. Berneis

[57] ABSTRACT

Compounds of the formula I:

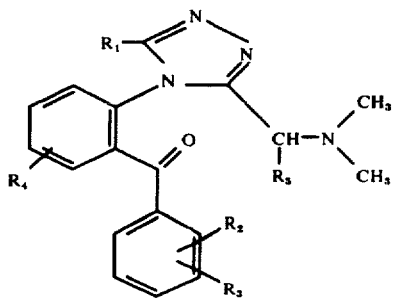

wherein $R_1$ is hydroxymethyl, or -$CH_2NR_6R_7$, in which $R_6$ is -$CH_2$-C ≡ CH, -$CH_2$-CH=$CH_2$,

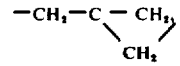

or alkyl of 1 to 3 carbon atoms, inclusive; $R_7$ is hydrogen or alkyl of 1 to 3 carbon atoms, or together

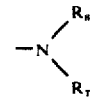

is pyrrolidino, piperidino or morpholino; wherein $R_2$ is hydrogen, chlorine or fluorine; wherein $R_3$ is hydrogen, or fluorine if $R_2$ is fluorine; wherein $R_4$ is hydrogen, fluorine, chlorine, bromine, nitro, or trifluoromethyl; and wherein $R_5$ is hydrogen, methyl or ethyl. These compounds, except those in which $R_7$ is hydrogen, are produced by heating a compound of formula II:

II wherein $R_2$, $R_3$, $R_4$, and $R_5$ are defined as hereinabove, and wherein $R'_1$ is the same as $R_1$ except that in defining $R'_1$, $R_7$ may not be hydrogen, with aqueous formaldehyde in formic acid solution at reflux temperature (about 100° C.).

Compounds in which $R_7$ are hydrogen require steps further shown in the specification.

The compounds of formula I and their pharmacologically acceptable acid addition salts thereof have tranquilizing, anti-anxiety and anti-convulsant activity useful for the treatment of animals and man.

14 Claims, No Drawings

[3-SUBSTITUTED-5-[(DI-METHYLAMINO)ME-THYL]-4H-1,2,4-TRIAZOL-4-YL]BENZOPHE-NONES AND PROCESS

BACKGROUND OF THE INVENTION

Field of the Invention

This invention is directed to novel organic compounds and is more specifically concerned with new 2-[3-substituted-5-[(dimethylamino)methyl]-4H-1,2,4-triazol-4-yl]benzophenones and a process of production therefor.

The novel compounds and the processes therefor can be illustratively represented as follows:

PROCESS I

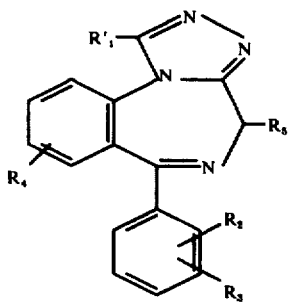

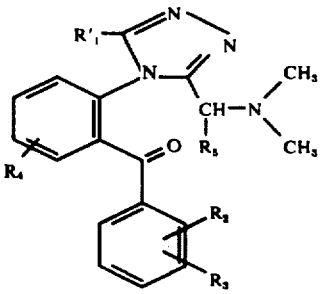

wherein R'$_1$ is hydroxymethyl or -CH$_2$NR$_6$R'$_7$, in which R$_6$ is -CH$_2$-C≡CH, -CH$_2$-CH=CH$_2$,

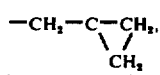

or alkyl of 1 to 3 carbon atoms, inclusive, R'$_7$ is alkyl of 1 to 3 carbon atoms, or together

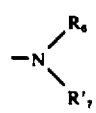

is pyrrolidino, piperidino or morpholino; wherein R$_2$ is hydrogen, chlorine or fluorine; wherein R$_3$ is hydrogen, or fluoro with the proviso that if R$_2$ is chloro, R$_3$ is not fluoro; wherein R$_4$ is hydrogen, fluorine, chlorine, bromine, nitro, or trifluoromethyl; and wherein R$_5$ is hydrogen, methyl or ethyl.

If a compound of formula IB

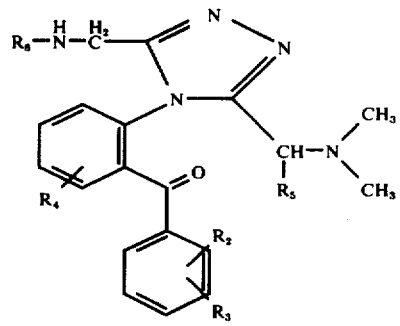

wherein R$_2$, R$_3$, R$_4$, R$_5$ and R$_6$ are defined as above, is wanted, the following process II may be used:

PROCESS II

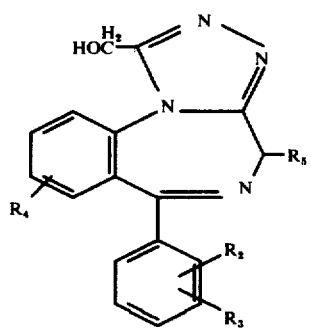

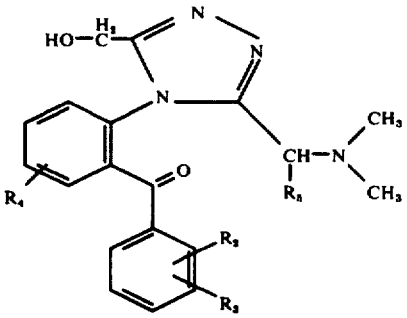

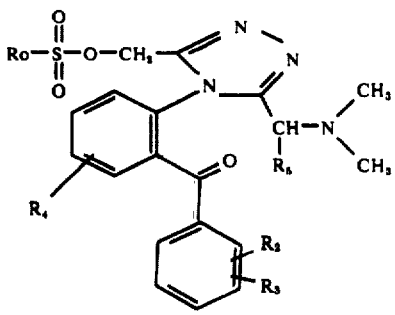

-continued

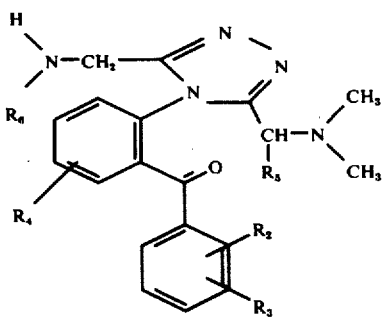
IB wherein $R_0$ is an organic radical selected from alkyl of 1 to 3 carbon atoms, phenyl and p-tolyl, and wherein $R_2$, $R_3$, $R_4$, $R_5$, and $R_6$ have the same values as hereinabove.

The compounds embraced by this invention can be presented by the formula I which combines structures IA and IB:

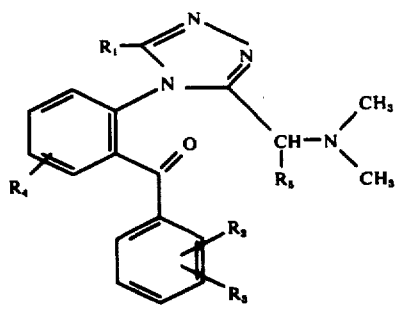
I wherein $R_1$ is hydroxymethyl, or $-CH_2NR_6R_7$, in which $R_6$ is $-CH_2-C\equiv CH$, $-CH_2-CH=CH_2$,

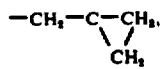

or alkyl of 1 to 3 carbon atoms, inclusive; $R_7$ is hydrogen or alkyl of 1 to 3 carbon atoms; or together

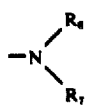

is pyrrolidino, piperidino or morpholino; wherein $R_2$ is hydrogen, chlorine or fluorine; wherein $R_3$ is hydrogen, or fluorine if $R_2$ is fluorine; wherein $R_4$ is hydrogen, fluorine, chlorine, bromine, nitro, or trifluoromethyl; and wherein $R_5$ is hydrogen, methyl, or ethyl, and the pharmacological acid addition salts thereof.

The invention also includes the pharmacologically acceptable acid addition salts of the compounds of formula I.

The more desirable compounds of this invention have the formula IC:

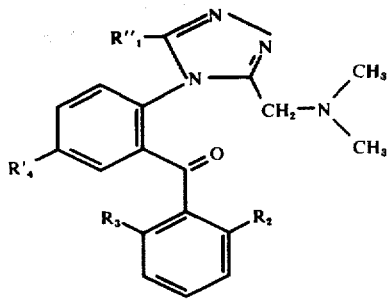
IC wherein $R''_1$ is hydroxymethyl or (dimethylamino)methyl; $R_2$ is hydrogen, chlorine, or fluorine; $R_3$ is hydrogen or fluorine if $R_2$ is fluorine and $R'_4$ is hydrogen, chlorine, or fluorine, and the pharmacologically acceptable acid addition salts thereof.

The most preferred compounds of this invention have the formula ID:

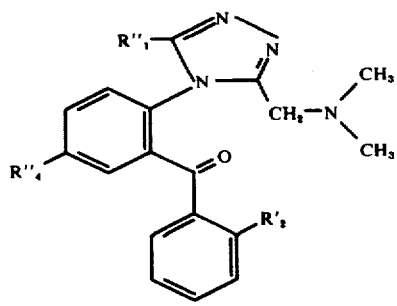
ID wherein $R''_1$ is hydroxymethyl or (dimethylamino)methyl; and wherein $R'_2$ and $R''_4$ are hydrogen or chlorine and the pharmacologically acceptable acid addition salts thereof.

The process I of this invention comprises: heating a compound of formula II in aqueous formic acid solution with 37% aqueous formaldehyde solution to give the corresponding compound of formula IA.

The process II of this invention comprises: treating a compound of formula IIA with formaldehyde in formic acid to obtain compound III; treating compound III with an organic sulfonyl chloride or an organic sulfonic anhydride with or without an added tertiary amine base to give compound IV; and treating compound IV with a primary amine to give the compound IB.

DESCRIPTION OF THE PREFERRED EMBODIMENT

Lower alkyl groups of 1 to 3 carbon atoms, inclusive, are exemplified by methyl, ethyl, and propyl.

The novel compounds of the formula I including the pharmacologically acceptable acid addition salts thereof have sedative, hypnotic, tranquilizing and muscle relaxant effects in mammals and birds.

The acid addition salts of compounds of formula I (including IA and IB) contemplated in this invention, are the hydrochlorides, hydrobromides, hydriodides, sulfates, phosphates, cyclohexanesulfamates, methanesulfonates and the like, prepared by reacting a compound of formula I with the stoichiometrically calculated amount of the selected pharmacologically acceptable acid.

The compounds of formula I can be given to mammals at a unit dosage of 0.05 to 10 mg./kg., preferably between 0.5 to 5 mg./kg., to produce sedation and tranquilization. For sleep induction the unit dosages are between 0.5 to 10 mg./kg. In larger mammals (over 10 kg.) the lower dosage ranges are adequate. Compounds of formula I are particularly useful in mammals such as cats, dogs, horses, or cattle during transportation by motor vehicles, railroad, boats, or planes.

Sedative (tranquilizing) effects of compounds of formula I are determined by the following tests:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1) running convulsions followed by (2) tonic extensor fits; followed by (3) death. The $ED_{50}$ is the dosage at which 50% of the mice are protected against (2) and (3).

The pharmaceutical forms contemplated by this invention include pharmaceutical compositions suited for oral, parenteral and rectal use, e.g., tablets, oils, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water or oil, e.g., coconut oil, sesame oil, safflower oil, cottonseed oil, peanut oil, may be used for preparing solutions or suspensions of the active drug. Sweetening, coloring and flavoring agents may be added.

The starting materials of formula II of this invention are produced as described in the preparations.

In carrying out process I of this invention a selected starting material of formula II structure is dissolved or suspended in formic acid and treated with formaldehyde. In the preferred embodiment 80–90% aqueous formic acid is used together with formaline (37% formaldehyde, balance water) and the thus obtained reaction mixture is heated from 50° C. to the reflux temperature of the mixture (about 100° C.), preferably in a nitrogen atmosphere. The formic acid and the formaldehyde are used in excess from 3 to 30 times mole equivalents per 1 mole equivalent of starting material. The time of reaction is from 1 to 48 hours. After the reaction is terminated, the mixture is neutralized with a base, e.g., aqueous sodium or potassium hydroxide and the product is recovered by extraction with a water-immiscible solvent such as methylene chloride, chloroform, ether or the like. The product is purified by conventional procedures, e.g., chromatography, crystallization or the like.

In carrying out process II of this invention, a selected starting material of formula IIA is dissolved or suspended in formic acid and treated with formaldehyde as described above for process I. The resulting product of formula III is dissolved in an inert organic solvent cooled to −20° C. to 0° C. and treated first with an organic sulfonyl chloride or an organic sulfonic anhydride to give compound IV. Compound IV may be isolated or reacted directly with an excess of a primary amine of the formula $R_6NH_2$ for 10–30 hours from 0° to 100° C. to yield compound IA. This product is purified by conventional procedures, e.g., chromatography, crystallization, or the like.

The following preparations and examples are illustrative of the processes and products of the present invention, but are not to be construed as limiting. Preparation 1 8-Chloro-1-(hydroxymethyl)-6-(o-chlorophenyl)-4H-s-triazolo[4,3-a][1,4]benzodiazepine A solution of 1,3-dihydro-7-chloro-5-(o-chlorophenyl)-2H-1,4-benzodiazepine-2-thione (9.63 g., 0.03 mole) and hydroxy-acetic acid hydrazide (6.66 g.) in n-butyl alcohol (300 ml.) is refluxed for about 15 hours with a slow stream of nitrogen bubbling through the reaction mixture for the first hour. The mixture is then cooled and concentrated in vacuo and the resulting residue is suspended in water, treated with a little ether and crystallized. The solid is collected by filtration and dried in vacuo. Recrystallization of this material from methylene chloride-methanol gives 8-chloro-1-(hydroxymethyl)-6-(o-chlorophenyl)-4H-s-triazolo[4,3-a][1,4]benzodiazepine in three crops: 4.96 g. of melting point 239°–241° C., 1.58 g. of melting point 236°–239° C., and 0.365 g. of melting point 232°–236° C. The analytical sample has a melting point of 239.5°–241° C. Anal. calcd. for $C_{17}H_{12}Cl_2N_4O$: C, 56.84; H, 3.37; Cl, 19.74; N, 15.60. Found: C, 56.27; H, 3.28; Cl, 19.75; N, 15.55. Preparation 2 8-Chloro-1-(hydroxymethyl)-6-phenyl-4H-s-triazolo[4,3-a][1,4]benzodiazepine In the manner given in Preparation 1, a solution of 1,3-dihydro-7-chloro-5-phenyl-2H-1,4-benzodiazepine-2-thione in n-butyl alcohol is heated to reflux with hydroxyacetic acid hydrazide to give 8-chloro-1-(hydroxymethyl)-6-phenyl-4H-s-triazolo[4,3-a][1,4]benzodiazepine of melting point 204°–206.5° C. Anal. calcd. for $C_{17}H_{13}ClN_4O$: C, 62.87; H, 4.03; Cl, 10.92; N, 17.25. Found: C, 62.66; H, 14.11; Cl, 10.93; N, 17.25. Preparation 3 8-Nitro-1-(hydroxymethyl)-6-(o-fluorophenyl)-4H-s-triazolo[4,3-a][1,4]benzodiazepine In the manner given in Preparation 1, a solution of 1,3-dihydro-7-nitro-5-(o-fluorophenyl)-2H-1,4-benzodiazepine-2-thione in n-butyl alcohol is heated to reflux with hydroxyacetic acid hydrazide to give 8-nitro-1-(hydroxymethyl)-6-(o-fluorophenyl)-4H-s-triazolo[4,3-a][1,4]benzodiazepine. Preparation 4 8-(Trifluoromethyl)-1-(hydroxymethyl)-6-(o-chlorophenyl)-4H-s-triazolo[4,3-a][1,4]benzodiazepine In the manner given in Example 1, a solution of 1,3-dihydro-7-trifluoromethyl-5-(o-chlorophenyl)-2H-1,4-benzodiazepine-2-thione and hydroxyacetic acid hydrazide in n-butyl alcohol is refluxed to give 8-trifluoromethyl-1-(hydroxymethyl)-6-(o-chlorophenyl)-4H-s-triazolo[4,3-a][1,4]benzodiazepine. Preparation 5 1-(Hydroxymethyl)-6-(o-chlorophenyl)-4H-s-triazolo[4,3-a][1,4]benzodiazepine In the manner given in Preparation 1, a solution of 1,3-dihydro-5-(o-chlorophenyl)-2H-1,4-benzodiazepine-2-thione and hydroxyacetic acid hydrazide in n-butyl alcohol is refluxed to give 1-(hydroxymethyl)-6-(o-chlorophenyl)-4H-s-triazolo[4,3-a][1,4]benzodiazepine. Preparation 6 8-Fluoro-1-(hydroxymethyl)-6-(o-chlorophenyl)-4H-s-triazolo[4,3-a][1,4]benzodiazepine In the manner given in Preparation 1, a solution of 1,3-dihydro-7-fluoro-5-(o-chlorophenyl)-2H-1,4-benzodiazepine-2-thione and hydroxyacetic acid hydrazide in n-butyl alcohol is refluxed to give 8-fluoro-1-(hydroxymethyl)-6-(o-chlorophenyl)-4H-s-triazolo[4,3-a][1,4]benzodiazepine. Preparation 7 8-Chloro-1-[(diethylamino)methyl]-6-phenyl-4H-s-triazolo[4,3-a][1,4]benzodiazepine In the manner given in Preparation 1, a solution of 1,3-dihydro-7-chloro-5-phenyl-2H-1,4-benzodiazepine-2-thione and (diethylamino)acetic acid hydrazide in n-butyl alcohol is reacted to give 8-chloro-1-[(diethyl amino)methyl]-6-phenyl-4H-s-triazolo[4,3-a][1,4]benzodiazepine, which is recrystallized from ethyl acetateSkellysolve B hexanes and has a melting point of 131.5°–132.5° C. Anal. calcd. for $C_{21}H_{22}ClN_5$: C, 66.39; H, 5.84; Cl, 9.33; N, 18.44. Found: C, 66.20; H, 6.06; Cl, 9.29; N, 18.55. Preparation 8 8-Nitro-1-[(diethylamino)methyl]-6-phenyl4H-s-triazolo[4,3-a][1,4]benzodiazepine In the manner given in Preparation 1, a solution of 1,3-dihydro-7-nitro-5-phenyl-2H-1,4-benzodiazepine-2thione in n-butyl alcohol is heated to reflux with (diethylamino)acetic acid acid hydrazide to give 8nitro-1-(diethylaminomethyl)-6-phenyl-4H-s-triazolo[4,3-a][1,4]benzodiazepine. Preparation 9 7-Chloro-5-phenyl-3H-1,4-benzodiazepin2-yl hydrazine A stirred mixture of 7-chloro-1,3-dihydro-5-phenyl-2H-1,4-benzodiazepine-2-thione (5- g., 0.174 mole) G.A. Archer, J. Org. Chem. 29 231 (1964) and methanol (1700 ml.) is treated with hydrazine hydrate (34.9 g.) and allowed to remain at ambient temperature for 1 hour 45 minutes. A slow stream of nitrogen is bubbled through the mixture during this period. The resulting solution is concentrated in vacuo at 25°–30° C. The thus obtained residue is mixed with water and extracted with chloroform. The extract is dried over anhydrous potassium carbonate and concentrated under reduced pressure on the rotary evaporator in such a manner that the chloroform is replaced by ethyl acetate. The resulting mixture is crystallized at 4° C. to give 26.6 g. of 7-chloro-5phenyl-3H-1,4-benzodiazepin-2-yl hydrazine of melting point 184°–186° C. and 3.04 g. of melting point 204°–211° C. (60%). This compound decomposes on heating in solvents to an unknown product, melting point 261°–262° C. The analytical sample is crystallized from ethyl acetate and has a melting point 217.5°–219° C. Anal. calcd. for $C_{15}H_{13}ClN_4$: C, 63.27; H, 4.60; Cl, 12.45; N, 19.68. Found: C, 63.30; H, 4.52; Cl, 12.46; N, 18.86. Preparation 10 8-Chloro-1-(chloromethyl)-6-phenyl-4H-s-triazolo[4,3-a][1,4]benzodiazepine 7-Chloro-5-phenyl-3H-1,4-benzodiazepin-2-yl hydrazine [14.2 g., 0.05 mole] is added slowly to acetic acid (150 ml.) with external cooling. A solution of chloroacetyl chloride (5.65 g.) in acetic acid (75 ml.) is then added during 10 minutes, and the red solution is stirred at ambient temperature for 1.5 hours, treated with sodium acetate (4.1 g.) stirred again for 30 minutes and then refluxed for 3 hours and 15 minutes. This mixture is cooled, poured into ice water and concentrated to a small volume. It is then diluted with water, neutralized with sodium bicarbonate and extracted with chloroform. The extract is dried over anhydrous magnesium sulfate, concentrated and the residue chromatographed on silica gel (1 kg.) with 1% methanol-99% chloroform. The product obtained from the column is crystallized from ethyl acetate to give 6.36 g. of 8-chloro-1-(chloromethyl)-6phenyl-4H-s-triazolo[4,3-a][1,4]benzodiazepine. The analytical sample has a melting point 183°–186.5° C. Anal. calcd. for $C_{17}H_{12}Cl_2N_4$: C, 59.49; H, 3.53; Cl. 20.66; N, 16.33. Found: C, 59.59; H, 3.31; Cl, 20.21; N, 16.42. Preparation 11 8-Chloro-1-(bromomethyl)-6-phenyl-4H-s-triazolo[4,3-a][1,4]benzodiazepine In the manner given in Preparation 10, 7-chloro-5-phenyl-3H-1,4-benzodiazepine-2-yl hydrazine is reacted with bromoacetyl chloride and after 1.5 hours with sodium acetate, then refluxed to give 8-chloro-1-(bromomethyl)6-phenyl-4H-s-triazolo[4,3-a][1,4]benzodiazepine. Preparation 12 8-Fluoro-1-(Chloromethyl)-6-(o-fluorophenyl)-4H-s-triazolo[4,3-a][1,4]benzodiazepine In the manner given in Preparation 10, 7-fluoro-5(o-fluorophenyl)-3H-1,4-benzodiazepin-2-yl hydrazine is reacted with chloroacetyl chloride and after 1.5 hours with sodium acetate. The mixture is then refluxed to give 8-fluoro-1-(chloromethyl)-6-(o-fluorophenyl)-4H-s-triazolo[4,3-a][1,4]benzodiazepine. Preparation 13 8-Chloro-1-(chloromethyl)-6-(2,6-difluorophenyl)-4H-s-triazolo[4,3-a][1,4]benzodiazepine In the manner given in Preparation 10, 7-chloro-5(2,6-difluorophenyl)-3H-1,4-benzodiazepin-2-yl hydrazine is reacted with chloroacetyl chloride and after 1.5 hours with sodium acetate, then the mixture is refluxed to give 8-chloro-1-(chloromethyl)-6-(2,6-difluorophenyl)-4H-s-triazolo[4,3-a][1,4-benzodiazepine. Preparation 14 8-Nitro-1-(bromomethyl)-6-(o-chlorophenyl)-4H-s-triazolo[4,3-a][1,4]benzodiazepine In the manner given in Preparation 10, 7-nitro-5(o-chlorophenyl)-3H-1,4-benzodiazepin-2-yl hydrazine is reacted with bromoacetyl bromide and after 1.5 hours with sodium acetate, then refluxed to give 8-nitro-1(bromomethyl)-6-(o-chlorophenyl)-4H-s-triazolo[4,3-a]-[1,4]benzodiazepine. Preparation 15 1-(Chloromethyl)-7-(trifluoromethyl)-6-(o-fluorophenyl)-4H-s-triazolo[4,3-a][1,4]benzodiazepine In the manner given in Preparation 10, 6-(trifluoromethyl)-5-(o-fluorophenyl)-3H-1,4-benzodiazepin-2-yl hydrazine is reacted with chloroacetyl chloride and after 1.5 hours with sodium acetate, then refluxed to give 1-(chloromethyl)-7-(trifluoromethyl)-6-(o-fluorophenyl)-4H-s-triazolo[4,3-a][1,4]benzodiazepine.

In the manner given in the prior preparations other 1-halomethyl-6-phenyl-4H-s-triazolo[4,3-a][1,4]-benzodiazepines can be prepared. Representative compounds, thus prepared, include:

1-(chloromethyl)-8-bromo-6-phenyl-4H-s-triazolo[4,3-a]-[1,4]benzodiazepine;

1-(chloromethyl)-10-fluoro-6-(o-fluorophenyl)-4H-s-triazolo[4,3-a][1,4]benzodiazepine;

1-(chloromethyl)-7-nitro-6-(m-chlorophenyl)-4H-s-triazolo[4,3-a][1,4]benzodiazepine;

1-(chloromethyl)-8-nitro-6-(2,6-difluorophenyl)-4H-s-triazolo[4,3-a][1,4]benzodiazepine;

1-(chloromethyl)-8-(trifluoromethyl)-6-(o-fluorophenyl)-4H-s-triazolo[4,3-a][1,4]benzodiazepine;

1-(chloromethyl)-8-chloro-6-phenyl-4-methyl-4H-s-triazolo[4,3-a][1,4]benzodiazepine;

1-(chloromethyl)-8-nitro-6-(o-chlorophenyl)-4-propyl4H-s-triazolo[4,3-a][1,4]benzodiazepine;

1-(chloromethyl)-7-(trifluoromethyl)-6-(m-fluorophenyl)-4-ethyl-4H-s-triazolo[4,3-a][1,4]benzodiazepine;

1-(chloromethyl)-8-chloro-6-(o-chlorophenyl)-4-methyl4H-s-triazolo[4,3-a][1,4]benzodiazepine; and the like.

From the 1-halomethyl-6-phenyl-4H-s-triazolo[4,3-a]-[1,4]benzodiazepine the corresponding 1-alkylaminomethyl, 1-allylaminomethyl, and 1-(2-propargylaminomethyl) compounds are obtained as shown by the following preparations:

Preparation 16 8-Chloro-1-[(dimethylamino)methyl]-6-phenyl-4H-s-triazolo[4,3-a][1,4]benzodiazepine An ice cold, stirred solution of 8-chloro-1-(chloromethyl)-6-phenyl-4H-s-triazolo[4,3-a][1,4]benzodiazepine (1.37 g., 0.004 mole) in tetrahydrofuran (40 ml.) is treated with a solution of dimethylamine in methanol (32 ml.) and potassium iodide (0.66 g.) and kept at ambient temperature (22°–24° C.) for 18 hours. The mixture is concentrated in vacuo and the residue is mixed with water, neutralized with a little sodium bicarbonate and extracted with chloroform. The extract is washed with brine, dried over anhydrous potassium carbonate and concentrated in vacuo. The residue is dissolved in ethyl acetate, decolorized with activated charcoal (Darco G60) and crystallized to give 0.937 g. of 8-chloro1-[(dimethylamino)methyl]-6-phenyl-4H-s-triazolo[4,3-a]-[1,4]benzodiazepine of melting point 171°–174° C. and 0.306 g. (88.3% yield), of melting point 171°–175° C. The analytical sample has a melting point 171°–172–5° C. Anal. calcd. for $C_{19}H_{18}ClN_5$: C, 64.86; H, 5.16; Cl, 10.08; N, 19.90. Found: C, 64.91; H, 5.35; Cl, 10.03; N, 19.53. Preparation 17 8-Chloro-1-[(dimethylamino)methyl]-6(o-chlorophenyl)-4H-s-triazolo[4,3-a][1,4]benzodiazepine A stirred mixture of 1-(chloromethyl)-8-chloro-6(o-chlorophenyl)-4H-s-triazolo[4,3-a][1,4]benzodiazepine (5.67 g., 0.015 mole) and dry tetrahydrofuran (150 ml.) is cooled in an ice bath and treated with methanolic dimethyl amine (15% v/v, 75 ml.) and potassium iodide (2.49 g.). The mixture is allowed to stand at room temperature under nitrogen for 18 hours. It is then concentrated and the residue is mixed with water and chloroform, neutralized with sodium bicarbonate and extracted with chloroform. The extract is washed with brine, dried over anhydrous sodium sulfate and concentrated in vacuo. The residue is crystallized from methanol-ethyl acetate to give in three crops:

1. 4.786 g. of melting point 202.5°–205° C. 2. 0.341 g. of melting point 201°–203° C. 3. 0.187 g. of melting point 202°–205° C. of 8-chloro-1-[(dimethylamino)-methyl]-6-(o-chlorophenyl)-4H-s-triazolo[4,3-a][1,4]benzodiazepine.

After two recrystallizations from methanol-ethyl acetate the product has a melting point of 203.5°–205° C. Anal. calcd. for $C_{19}H_{17}Cl_2N_5$: C, 59.08; H, 4.44; Cl, 18.36; N, 18.13; Found: C, 59.12; H, 4.47; Cl, 18.59; N, 17.80 Preparation 18 1-[(Dimethylamino)methyl]-6-(o-chlorophenyl)-4H-s-triazolo[4,3-a][1,4]benzodiazepine A stirred mixture of 1-(chloromethyl)-6-(o-chlorophenyl)-4H-s-triazolo[4,3-a][1,4]benzodiazepine (5.14 g., 0.015 mole) in dry tetrahydrofuran (150 ml.) is cooled in an ice bath and treated with a 15% (v/v) solution of dimethylamine in methanol (75 ml.) and potassium iodide (2.49 g.). The mixture is stirred under nitrogen at ambient temperature for 18 hours and concentrated in vacuo. The residue is mixed with water and chloroform, neutralized with sodium bicarbonate, and extracted with chloroform. The extract is washed with brine, drier over anhydrous sodium sulfate and concentrated in vacuo. The residue is crystallized from ethyl acetate-Skellysolve B hexanes to give 4.43 g. of 1-[(dimethylamino)methyl]-6-(o-chlorophenyl)-4H-s-triazolo[4,3-a][1,4]benzodiazepine of melting point 143°–145° C.

A sample of this material which is recrystallized from ethyl acetate-Skellysolve B hexanes for analysis has a melting point of 143°–146° C.

Anal. Calcd. for $C_{19}H_{18}ClN_5$: C, 64.86; H, 5.16; Cl, 10.08; N, 19.90. Found: C, 64.70; H, 5.09; Cl, 10.11; N, 20.00. Preparation 19 8-Chloro-1-[[(2-propynyl)amino]methyl]-6-phenyl-4H-s-triazolo[4,3-a][1,4]benzodiazepine A stirred mixture of 1-(chloromethyl)-8-chloro-6-phenyl-4H-s-traizolo[4,3-a][1,4]benzodiazepine (3.43 g., 0.01 mole), potassium iodide (1.66 g., 0.01 mole), propargyl amine (1.10 g., 0.02 mole) and dimethyl formamide (50 ml.) is kept at ambient temperature, under nitrogen, for 12 hours, and concentrated in vacuo. The residue is mixed with water and extracted with methylene chloride. The extract is washed with water, dried over anhydrous sodium sulate, and concentrated. Crystallization of the residue from methanol ethyl acetate gives a small amount of a solid of melting point 155°–158° C. dec. The mother liquor is concentrated and chromatographed on silica gel (300 g.) with a mixture of 2.5% methanol97.5% chloroform. The product thus obtained is crystallized from methylene chloride to give 1.62 g. of 8-chloro-1-[[(2-propynyl)amino]methyl]-6-phenyl-4H-s-triazolo[4,3-a][1,4]benzodiazepine of melting point 193°–195.5° C. and 0.38 g., of melting point 190°–194° C. The analytical sample has melting point 193°–195.5° C. Anal. calcd. for $C_{20}H_{16}ClN_5$: C, 66.39; H, 4.46; Cl, 9.80; N, 19.36. Found: C, 66.27; H, 4.54; Cl, 10.05; N, 19.66. Preparation 20 8-Chloro-1-[[(2-propynyl)amino]methyl]-6-(o-chlorophenyl)-4H-s-triazolo[4,3-a][1,4]benzodiazepine In the manner given in Preparation 19, 8-chloro-1-(chloromethyl)-6-(o-chlorophenyl)-4H-s-triazolo[4,3-a]-[1,4]benzodiazepine in dimethylformamide is reacted at room temperature with propargylamine in the presence of potassium iodide to give 8-chloro-1-[[(2-propynyl)amino[methyl]-6-(o-chlorophenyl)-4H-s-triazolo[4,3-a][1,4]benzodiazepine. Preparation 21 8-Fluoro-1-[[(2-propynyl)amino]methyl]-6-(o-chlorophenyl)-4H-s-triazolo[4,3-a][1,4]benzodiazepine In the manner given in Preparation 19, 8-fluoro-1-(bromomethyl)-6-(o-chlorophenyl)-4H-s-triazolo[4,3-a][1,4]-benzodiazepine in dimethylformamide is reacted at room temperature with propargylamine in the presence of potassium iodide to give 8-fluoro-1-[[(2-propynyl)amino]methyl]-6-(o-chlorophenyl)-4H-s-triazolo[4,3-a][1,4]benzodiazepine. Preparation 22 8-(Trifluoromethyl)-1-[[(2-propynyl)amino]methyl]-

6-(o-chlorophenyl)-4H-s-triazolo[4,3-a][1,4]benzodiazepine

In the manner given in Preparation 19, 8 -(trifluoromethyl)-1-(chloromethyl)-6-(o-chlorophenyl)-4H-s-triazolo[4,3-a][1,4]benzodiazepine in dimethylformamide is reacted at room temperature with propargylamine in the presence of potassium iodide to give 8-(trifluoromethyl)-1-[[(2-propynyl)amino]methyl]-6-(o-chlorophenyl)-4H-s-triazolo[4,3-a][1,4]benzodiazepine. Preparation 23 8 -Chloro-1-[[(2-propynyl)amino]methyl]-6-(2,6-difluorophenyl)-4H-s-triazolo[4,3-a][1,4]benzodiazepine In the manner given in Preparation 19, 8 -chloro-1-(chloromethyl)-6-(2,6-difluorophenyl)-4H-s-triazolo[4,3-a][1,4]benzodiazepine in dimethylformamide is reacted at room temperature with propargylamine in the presence of potassium iodide to give 8-chloro-1-[[(2-propynyl)amino]methyl]-6-(2,6-difluorophenyl)-4H-s-triazolo[4,3-a][1,4]benzodiazepine. Preparation 24 8 -Nitro-1-[[(2-propynyl)amino]-methyl]-6(o-chlorophenyl)-4H-s-triazolo[4,3-a][1,4]benzodiazepine In the manner given in Preparation 19, 8 -nitro-1-(bromomethyl)-6-(o-chlorophenyl)-4H-s-triazolo[4,3-a][1,4]benzodiazepine in dimethylformamide is reacted at room temperature with propargylamine in the presence of potassium iodide to give 8-nitro-1-[[(2-propynyl)amino] methyl]-6-(o-chlorophenyl)-4H-s-triazolo[4,3-a][1,4]benzodiazepine. Preparation 25 8 -Chloro-1-[[(cyclopropylmethyl)amino]methyl]-6-phenyl-4H-s-triazolo[4,3-a][1,4]benzodiazepine A stirred mixture of 8-chloro-1-(chloromethyl)-6-phenyl-4H-s-triazolo[4,3-a][1,4]benzodiazepine (1.37 g., 0.004 mole), potassium iodide (0.67 g., 0.004 mole), (cyclopropylmethyl)amine (0.685 g., 0.012 mole) and tetrahydrofuran (100 ml.) is kept under nitrogen at ambient temperature (25° C.) for 18 hours and then concentrated in vacuo. The residue is mixed with water and extracted with methylene chloride. The extract is washed with brine, dried over anhydrous sodium sulfate and concentrated. The residual oil is dissolved in methylene chloride-methanol-chloroform, treated with Darco (G 60) and silica gel and filtered through Celite (diatomacious earth). The filtrate is concentrated and crystallized from ethyl acetate to give 0.72 g. of 8-chloro-1-[[(cyclopropylmethyl)amino]methyl]-6-phenyl-4H-s-triazolo[4,3-a][1,4]benzodiazepine of melting point 164°–169° C. The analytical sample has a melting point of 165°–171° C. Anal. calcd. for $C_{20}H_{18}ClN_5$: C, 66.02; H, 4.99; Cl, 9.74; N, 19.25. Found: C, 65.77; H, 5.11; Cl, 9.87; N, 19.15. Preparation 26 8 -Nitro-1-[[(cyclopropylmethyl)amino]methyl]-6-phenyl-4H-s-triazolo[4,3-a][1,4]benzodiazepine A stirred mixture of 8-nitro-1-(chloromethyl)-6-phenyl-4H-s-triazolo[4,3-a][1,4]benzodiazepine (0.004 mole), potassium iodide (0.67 g., 0.004 mole), (cyclopropylmethyl)amine (0.84 g., 0.012 mole) and tetrahydrofuran (100 ml.) is kept at ambient temperature (25° C.) for 18 hours and then concentrated in vacuo. The residue is mixed with water and extracted with methylene chloride. The extract is washed with brine, dried over anhydrous sodium sulfate and concentrated. The residue is crystallized from ethyl acetate-Skellysolve B hexanes to give 8-nitro-1-[[(cyclopropylmethyl)amino]methyl]-6-phenyl-4H-s-triazolo[4,3][1,4]benzodiazepine. Preparation 27 8-(Trifluoromethyl)-1-[[(cyclopropylmethyl)amino]methyl]-6-(o-chlorophenyl)-4H-s-triazolo[4,3-a][1,4]benzodiazepine A stirred solution of potassium hydroxide (3.37 g., 0.06 mole) in methanol (30 ml.) is cooled in an ice bath, under nitrogen, and treated with (cyclopropylmethyl)-amine hydrochloride (6.45 g., 0.06 mole). The resulting mixture is kept in the ice bath for 15 minutes, treated with tetrahydrofuran (250 ml.), 8-(trifluoromethyl)-1-(chloromethyl)-6-(o-chlorophenyl)-4H-s-triazolo[4,3-a][1,4]benzodiazepine (6.86 g., 0.02 mole) and potassium iodide (3.32 g., 0.02 mole) and kept at ambient temperature for 18 hours. The mixture is concentrated and the residue is mixed with water and extracted with methylene chloride. The extract is washed with brine, dried over anhydrous sodium sulfate and concentrated. The product is crystallized once from ethyl acetate and once from methylene chloride ethyl acetate to give 8-(trifluoromethyl)-1-[[(cyclopropylmethyl)amino]methyl]-6-(o-chlorophenyl)-4H-s-triazolo[4,3-a][1,4]benzodiazepine. Preparation 28 8 -Chloro-1-[[(cyclopropylmethyl)amino] methyl]-6-(o-chlorophenyl)-4H-s-triazolo[4,3-a][1,4]benzodiazepine In the manner given in Preparation 25, 8-chloro-1-(chloromethyl)-6-(o-chlorophenyl)-4H-s-triazolo[4,3-a][1,4]benzodiazepine is treated with (cyclopropylmethyl)amine in tetrahydrofuran at room temperature to give 8-chloro-1-[[(cyclopropylmethyl)amino]methyl]-6-(o-chlorophenyl)-4H-s-triazolo[4,3-a][1,4]benzodiazepine. Preparation 29 8 -Chloro-1-[[(cyclopropylmethyl)methylamino]methyl]-6-phenyl-4H-s-triazolo[4,3-a][1,4]benzodiazepine A stirred mixture of 8-chloro-1-(chloromethyl)-6-phenyl-4H-s-triazolo[4,3-a][1,4]benzodiazepine (1.37 g., 0.004 mole), potassium iodide (0.67 g., 0.004 mole), methyl(cyclopropylmethyl)amine (1.02 g., 0.012 mole) and tetrahydrofuran (100 ml.) is kept at ambient temperature (25° C.) for 18 hours and concentrated in vacuo. The extract is washed with brine, dried over anhydrous sodium sulfate and concentrated. The residue is crystallized from ethyl acetate and methylene chlorideethyl acetate to give 8-chloro-1-[[(cyclopropylmethyl)methylamino]methyl]-6-phenyl-4H-s-triazolo[4,3-a][1,4]benzodiazepine. Preparation 30 8 -Chloro-1-[[(cyclopropylmethyl)-methylamino]methyl]-6-(o-chlorophenyl)-4H-s-triazolo[4,3-a][1,4]benzodiazepine In the manner given in Preparation 29, potassium iodide and 8-chloro-1-(chloromethyl)-6-(o-chlorophenyl)-4H-s-triazolo[4,3-a][1,4]benzodiazepine in tetrahydrofuran are treated with methyl(cyclopropylmethyl)amine to give 8-chloro-1-[[(cyclopropylmethyl)methylamino]methyl]-6-(o-chlorophenyl)-4H-s-triazolo[4,3-a][1,4]-benzodiazepine. Preparation 31 8-Bromo-1-[[(cyclopropylemethyl)ethylamino]methyl]-6-phenyl-4H-s-triazolo[4,3-a][1,4]benzodiazepine In the manner given in Preparation 29, 8-bromo-1-(chloromethyl)-6-phenyl-4H-s-triazolo[4,3-a][1,4]benzodiazepine is treated with ethyl(cyclopropylmethyl)amine to give 8-bromo-1-[[(cyclopropylmethyl)ethylamino]methyl]-6-phenyl-4H-s-triazolo[4,3-a][1,4]benzodiazepine. Preparation 32 8-(Trifluoromethyl)-1-[[(cyclopropylmethyl)methylamino]methyl]-6-(o-chlorophenyl)-4H-s-triazolo[4,3-a][1,4]benzodiazepine In the manner given in Preparation 29, 8-(trifluoromethyl)-1-(chloromethyl)-6-(o-chlorophenyl)-

4H-s-triazolo[4,3-a][1,4]benzodiazepine is treated with methyl(cyclopropylmethyl)amine to give 8-(trifluoromethyl)-1-[[(cyclopropylmethyl)methylamino]methyl]-6-(o-chlorophenyl)-4H-s-triazolo[4,3-a][1,4]benzodiazepine. Preparation 33 8-Chloro-1-[[(cyclopropylmethyl)propylamino]methyl]-6-(2,6-difluorophenyl)-4H-s-triazolo[4,3-a][1,4]benzodiazepine In the manner given in Preparation 29, 8-chloro-1-(chloromethyl)-6-(2,6-difluorophenyl)-4H-s-triazolo[4,3-a][1,4]benzodiazepine is treated with propyl(cyclopropylmethyl)amine to give 8-chloro-1-[[(cyclopropylmethyl)propylamino]methyl]-6-(2,6-difluorophenyl)-4H-s-triazolo[4,3-a][1,4]benzodiazepine. Preparation 34 8-Nitro-1-[[(cyclopropylmethyl)propylamino]methyl]-6-phenyl-4-H-s-triazolo[4,3-a][1,4]-benzodiazepine In the manner given in Preparation 29, 8-nitro-1-(chloromethyl)-6-phenyl-4H-s-triazolo[4,3-a][1,4]benzodiazepine is treated with propyl(cyclopropylmethyl)-amine to give 8-nitro-1-[[(cyclopropylmethyl)propylamino]methyl]-6-phenyl-4H-s-triazolo[4,3-a][1,4]benzodiazepine. Preparation 35 8-Fluoro-1-[[(cyclopropylmethyl)ethylamino]methyl]-6-(o-fluorophenyl)-4H-s-triazolo[4,3-a][1,4]benzodiazepine In the manner given in Preparation 29, 8-fluoro-1-(chloromethyl)-6-(o-fluorophenyl)-4H-s-triazolo[4,3-a][1,4]benzodiazepine is treated with ethyl(cyclopropylmethyl)amine to give 8-fluoro-1-[[(cyclopropylmethyl)ethylamino]methyl]-6-(o-fluorophenyl)-4-H-s-triazolo[4,3-a][1,4]benzodiazepine. Preparation 36 9-(Trifluoromethyl)-1-[[(cyclopropylmethyl)methylamino]methyl]-6-phenyl-4-H-s-triazolo[4,3-a][1,4]benzodiazepine In the manner given in Preparation 29, 9-(trifluoromethyl)-1-(chloromethyl)-6-phenyl-4H-s-triazolo[4,3-a]-[1,4]benzodiazepine is treated with methyl(cyclopropylmethyl)amine to give 8-(trifluoromethyl)-1-[[(cyclopropylmethyl)methylamino]methyl]-6-phenyl-4-H-s-triazolo[4,3-a][1,4]benzodiazepine. Preparation 37 8-Chloro-1-[(allylamino)methyl]-6-phenyl-4H-s-triazolo[4,3-a][1,4]benzodiazepine A stirred mixture of 8-chloro-1-(chloromethyl)-6-phenyl-4H-s-triazolo[4,3-a][1,4]benzodiazepine (1.37 g., 0.004 mole), potassium iodide (0.67 g., 0.004 mole), allylamine (0.685 g., 0.012 mole) and tetrahydrofuran (100 ml.) is kept at ambient temperature (25° C.) for 18 hours and then concentrated in vacuo. The residue is mixed with water and extracted with methylene chloride. The extract is washed with brine, dried over anhydrous sodium sulfate and concentrated. The residue is crystallized once from ethyl acetate-Skellysolve B hexanes and then from methylene chloride-ethyl acetate-Skellysolve B hexanes to give 0.495 g. of 8-chloro-1-[(allylamino)-methyl]-6-phenyl-4H-s-triazolo[4,3-a][1,4]benzodiazepine of melting point 127°-129° C. The analytical sample has a melting point of 128°-132° C. Anal. cacd. for $C_{20}H_{18}ClN_5$: C, 66.02; H, 4.99; Cl, 9.74; N, 19.25. Found: C, 66.09; H, 5.12; Cl, 9.63; N, 19.19. Preparation 38 8-Chloro-1-[(allylamino)methyl]-6-(o-chlorophenyl)-4H-s-triazolo[4,3-a][1,4]benzodiazepine A stirred mixture of 8-chloro-1-(chloromethyl)-6-(o-chlorophenyl)-4H-s-triazolo[4,3-a][1,4]benzodiazepine (0.004 mole), potassium iodide (0.67 g., 0.004 mole), allylamine (0.84 g., 0.012 mole) and tetrahydrofuran (100 ml.) is kept at ambient temperature (25° C.) for 18 hours and then concentrated in vacuo. The residue is mixed with water and extracted with methylene chloride. The extract is washed with brine, dried over anhydrous sodium sulfate and concentrated. The residue is crystallized from ethyl acetate-Skellysolve B hexanes to give 8-chloro-1-[(allylamino)methyl]-6-(o-chlorophenyl)-4H-s-triazolo[4,3-a][1,4]benzodiazepine. Preparation 39 8-Chloro-1-[(allylmethylamino)-methyl]-6-phenyl-4H-s-triazolo[4,3-a][1,4]benzodiazepine A stirred mixture of 8-chloro-1-(chloromethyl)-6-phenyl-4-H-s-triazolo[4,3-a][1,4]benzodiazepine (1.37 g., 0.004 mole), potassium iodide (0.67 g., 0.004 mole), methylallylamine (0.84 g., 0.012 mole) and tetrahydrofuran (100 ml.) is kept at ambient temperature (25° C.) for 18 hours and concentrated in vacuo. The residue is mixed with water and extracted with methylene chloride. The extract is washed with brine, dried over anhydrous sodium sulfate and concentrated. The residue is crystallized from ethyl acetate-Skellysolve B hexanes to give 1.19 g of 8-chloro-1-[(allylmethylamino)methyl]-6-phenyl-4H-s-triazolo[4,3-a][1,4]benzodiazepine of melting point 157°–160° C. The analytical sample has a melting point of 158°–164° C. Anal. calcd. for $C_{21}H_{20}ClN_5$: C, 66.75; H, 5.33; Cl, 9.38; N, 18.53. Found: C, 66.87; H, 5.46; Cl, 9.42; N, 18.67. Preparation 40 8-Chloro-1-[(allylmethylamino)methyl]-6-(o-chlorophenyl)-4H-s-triazolo[4,3-a][1,4]benzodiazepine In the manner given in Preparation 39, 8-chloro-1-(chloromethyl)-6-(o-chlorophenyl)-4H-s-triazolo[4,3-a][1,4]benzodiazepine, potassium iodide, and methylallylamine in tetrahydrofuran are reacted to give 8-chloro-1-[(allylmethylamino)methyl]-6-(o-chlorophenyl)-4-H-s-triazolo [4,3-a][1,4]benzodiazepine. Preparation 41 8-Nitro-1-[(allylmethylamino)methyl]-6-(o-chlorophenyl)-4-H-s-triazolo[4,3-a][1,4]benzodiazepine In the manner given in Preparation 39, 8-nitro-1-(chloromethyl)-6-(o-chlorophenyl)-4H-s-triazolo[4,3-a]-[1,4]benzodiazepine, potassium iodide, and methylallylamine in tetrahydrofuran are reacted to give 8-nitro-1-[(allylmethylamino)methyl]-6-(o-chlorophenyl)-4H-s-triazolo[4,3-a][1,4]benzodiazepine. Preparation 42 8-Bromo-1-[(allylethylamino)methyl]-6-phenyl-4H-s-triazolo[4,3-a][1,4]benzodiazepine In the manner given in Preparation 39, 8-bromo-1-(chloromethyl)-6-phenyl-4H-s-triazolo[4,3-a][1,4]benzodiazepine, potassium iodide and ethylallylamine in tetrahydrofuran are reacted to give 8-bromo-1-[(allylethylamino)methyl]-6-phenyl-4H-s-triazolo[4,3-a][1,4]benzodiazepine. Preparation 43 8-(Trifluoromethyl)-1-[(allylmethylamino)methyl]-6-(o-chlorophenyl)-4H-s-triazolo[4,3-a][1,4]benzodiazepine In the manner given in Preparation 39, 8-(trifluoromethyl)-1-(chloromethyl)-6-(o-chlorophenyl)-4H-s-triazolo[4,3-a][1,4]benzodiazepine, potassium iodide and methylallylamine in tetrahydrofuran are reacted to give 8-(trifluoromethyl)-1-[(allylmethylamino)methyl]-6-(o-chlorophenyl)-4H-s-triazolo[4,3-a][1,4]benzodiazepine. Preparation 44 8-Chloro-1-[(allylpropylamino)methyl]-6-(2,6-difluorophenyl)-4H-s-triazolo[4,3-a][1,4]benzodiazepine In the manner given in Preparation 39, 8-chloro-1-(chloromethyl)-6-(2,6-difluorophenyl)-4H-s-triazolo-

[4,3-a][1,4]benzodiazepine, potassium iodide and propylallylamine in tetrahydrofuran are reacted to give 8-chloro-1-[(allylpropylamino)methyl]-6-(2,6-difluorophenyl)-4H-s-triazolo[4,3-a][1,4]benzodiazepine. Preparation 45 8-Nitro-1-[(allylpropylamino)methyl]-6-phenyl-4H-s-triazolo[4,3-a][1,4]benzodiazepine In the manner given in Preparation 39, 8-nitro-1-(chloromethyl)-6-phenyl-4H-s-triazolo[4,3-a][1,4]benzodiazepine, potassium iodide and propylallylamine in tetrahydrofuran are reacted to give 8-nitro-1-[(allylpropylamino)methyl]-6-phenyl-4H-s-triazolo[4,3-a][1,4]benzodiazepine. Preparation 46 8-Fluoro-1-[(allylethylamino)methyl]-6-(o-fluorophenyl)-4H-s-triazolo[4,3-a][1,4]benzodiazepine In the manner given in Preparation 39, 8-fluoro-1-(chloromethyl)-6-(o-fluorophenyl)-4H-s-triazolo[4,3-a][1,4]benzodiazepine, potassium iodide and ethylallylamine in tetrahydrofuran are reacted to give 8-fluoro-1-[(allylethylamino)methyl]-6-(o-fluorophenyl)-4H-s-triazolo[4,3-a][1,4]benzodiazepine. Preparation 47 9-(Trifluoromethyl)-1-[(allylmethylamino)methyl]-6-phenyl-4H-s-triazolo[4,3-a][1,4]benzodiazepine In the manner given in Preparation 39, 9-(trifluoromethyl)-1-(chloromethyl)-6-phenyl-4H-s-triazolo[4,3-a]-[1,4]benzodiazepine, potassium iodide and methylallylamine in tetrahydrofuran are reacted to give 9-(trifluoromethyl)-1-[(allylmethylamino)methyl]-6-phenyl-4H-s-triazolo[4,3-a][1,4]benzodiazepine. Preparation 48 8-Chloro-1-(pyrrolidinomethyl)-6-phenyl-4H-s-triazolo[4,3-a][1,4]benzodiazepine A stirred mixture of 8-chloro-1-(chloromethyl)-6-phenyl-4H-s-triazolo[4,3-a][1,4]benzodiazepine (1.37 g., 0.004 mole), potassium iodide (0.67 g., 0.004 mole), pyrrolidine (0.853 g., 0.012 mole) and tetrahydrofuran (100 ml.) is kept at ambient temperature (25° C.) for 18 hours and then concentrated in vacuo. The residue is mixed with water and extracted with methylene chloride. The extract is washed with brine, dried over anhydrous sodium sulfate and concentrated. The residue is crystallized to give 8-chloro-1-(pyrrolidinomethyl)-6-phenyl-4H-s-triazolo[4,3-a][1,4]benzodiazepine.

Preparation 49
8-Chloro-1-(pyrrolidinomethyl)-6-(o-chlorophenyl)-4H-s-triazolo[4,3-a][1,4]benzodiazepine In the manner given in Preparation 48, 8-chloro-1-(chloromethyl)-6-(o-chlorophenyl)-4H-s-triazolo[4,3-a]-[1,4]benzodiazepine, potassium iodide, and pyrrolidine in tetrahydrofuran are reacted to give 8-chloro-1-(pyrrolidinomethyl)-6-(o-chlorophenyl)-4H-s-triazolo[4,3-a][1,4]benzodiazepine.

In the manner given in Preparation 48, 8-(trifluoromethyl)-1-(chloromethyl)-6-phenyl-4H-s-triazolo[4,3-a][1,4]benzodiazepine, potassium iodide, and pyrrolidine in tetrahydrofuran are reacted to give 8-(trifluoromethyl)-1-(pyrrolidinomethyl)-6-phenyl-4H-s-triazolo[4,3-a][1,4]-benzodiazepine.

Preparation 51
8-Chloro-1-(piperidinomethyl)-6-phenyl-4H-s-triazolo[4,3-a][1,4]benzodiazepine In the manner given in Preparation 48, 8-chloro-1-(chloromethyl)-6-phenyl-4H-s-triazolo[4,3-a][1,4]benzodiazepine, potassium iodide, and piperidine in tetrahydrofuran are reacted to give 8-chloro-1-(piperidinomethyl)-6-phenyl-4H-s-triazolo[4,3-a][1,4]benzodiazepine.

Preparation 52
8-Fluoro-1-(piperidinomethyl)-6-phenyl-4H-s-triazolo[4,3-a][1,4]benzodiazepine

In the manner given in Preparation 48, 8-fluoro-1-(chloromethyl)-6-phenyl-4H-s-triazolo[4,3-a][1,4]benzodiazepine, potassium iodide, and piperidine in tetrahydrofuran are reacted to give 8-fluoro-1-(piperidinomethyl)-6-phenyl-4H-s-triazolo[4,3-a][1,4]benzodiazepine.

Preparation 53
8-Chloro-1-(morpholinomethyl)-6-(o-chlorophenyl)-4H-s-triazolo[4,3-a][1,4]benzodiazepine In the manner given in Preparation 48, 8-chloro-1-(chloromethyl)-6-(o-chlorophenyl)-4H-s-triazolo[4,3-a]-[1,4]benzodiazepine, potassium iodide, and morpholine in tetrahydrofuran are reacted to give 8-chloro-1-(morpholinomethyl)-6-(o-chlorophenyl)-4H-s-triazolo[4,3-a][1,4]benzodiazepine.

Preparation 54
8-Nitro1-1-(morpholinomethyl)-6-phenyl-4H-s-triazolo[4,3-a][1,4]benzodiazepine In the manner given in Preparation 48, 8-nitro-1-(chloromethyl)-6-phenyl-4H-s-triazolo[4,3-a][1,4]benzodiazepine, potassium iodide, and morpholine in tetrahydrofuran are reacted to give 8-nitro-1-(morpholinomethyl)-6-phenyl-4H-s-triazolo[4,3-a][1,4]benzodiazepine.

Preparation 55
8-Bromo-1-(morpholinomethyl)-6-(o-chlorophenyl)-4H-s-triazolo[4,3-a][1,4]benzodiazepine In the manner given in Preparation 48, 8-bromo-1-(chloromethyl)-6-(o-chlorophenyl)-4H-s-triazolo[4,3-a][1,4]benzodiazepine, potassium iodide, and morpholine in tetrahydrofuran are reacted to give 8-bromo-1-(morpholinomethyl)-6-(o-chlorophenyl)-4H-s-triazolo[4,3-a][1,4]benzodiazepine.

In the manner given in the previous preparations, other starting materials of formulae 11 and 11A can be prepared. Such starting materials comprise:
  8-bromo-1-(hydroxymethyl)-6-phenyl-4H-s-triazolo[4,3-a]-[1,4]benzodiazepine;
  8-chloro-1-(hydroxymethyl)-6-(2,6-difluorophenyl)-4H-s-triazolo[4,3-a][1,4]benzodiazepine;
  8-fluoro-1-(hydroxymethyl)-6-(o-fluorophenyl)-4H-s-triazolo[4,3-a][1,4]benzodiazepine;
  8-chloro-1-(hydroxymethyl)-4-methyl-6-phenyl-4H-s-triazolo[4,3-a][1,4]benzodiazepine;
  9-bromo-1-(hydroxymethyl)-4-propyl-6-phenyl-4H-s-triazolo[4,3-a][1,4]benzodiazepine;
  8-nitro-1-(hydroxymethyl)-4-ethyl-6-(o-chlorophenyl)-4H-s-triazolo[4,3-a][1,4]benzodiazepine;
  8-chloro-1-[[(2-propynyl)ethylamino]methyl]-6-phenyl-4H-s-triazolo[4,3-a][1,4]benzodiazepine;
  8-fluoro-1-[[(2-propynyl)propylamino]methyl]-6-phenyl-4H-s-triazolo[4,3-a][1,4]benzodiazepine;
  8-bromo-1-[[(2-propynyl)ethylamino]methyl]-6-(o-chlorophenyl)-4H-s-triazolo[4,3-a][1,4]benzodiazepine;
  8-chloro-1-[[(2-propynyl)propylamino]methyl]-6-(2,6-difluorophenyl)-4H-s-triazolo[4,3-a][1,4]benzodiazepine;

8-(trifluoromethyl)-1-[[(2-propynyl)methylamino]methyl]-4-propyl-6-phenyl-4H-s-triazolo[4,3-a][1,4]benzodiazepine;

9-nitro-1-[[(2-propynyl)ethylamino]methyl]-4-methyl-6-phenyl-4H-s-triazolo[4,3-a][1,4]benzodiazepine;

8-chloro-1-[[(2-propynyl)methylamino]methyl]-4-ethyl-6-(m-chlorophenyl)-4H-s-triazolo[4,3-a][1,4]benzodiazepine;

7-(trifluoromethyl)-1-[[(2-propynyl)propylamino]methyl]4-methyl-6-(p-chlorophenyl)-4H-s-triazolo[4,3-a][1,4]benzodiazepine;

8-nitro-1-[[(cyclopropylmethyl)ethylamino]methyl]-6-(o-chlorophenyl)-4H-s-triazolo[4,3-a][1,4]benzodiazepine;

8-chloro-1-[[(cyclopropylmethyl)methylamino]methyl]-4-methyl-6-(o-chlorophenyl)-4H-s-triazolo[4,3-a][1,4]benzodiazepine;

9-chloro-1-[[(cyclopropylmethyl)amino]methyl]-4-ethyl-6-(m-chlorophenyl)-4H-s-triazolo[4,3-a][1,4]benzodiazepine;

9-bromo-1-[[(cyclopropylmethyl)propylamino]methyl]-6-(o-chlorophenyl)-4H-s-triazolo[4,3-a][1,4]benzodiazepine;

7-chloro-1-[[(cyclopropylmethyl)ethylamino]methyl]-6-(o-fluorophenyl)-4H-s-triazolo[4,3-a][1,4]benzodiazepine;

10-(trifluoromethyl)-1-[[(cyclopropylmethyl)methylamino]methyl]-6-(o-chlorophenyl)-4H-s-triazolo[4,3-a][1,4]benzodiazepine;

9-chloro-1-[[(cyclopropylmethyl)methylamino]methyl]-6-(o-chlorophenyl)-4H-s-triazolo[4,3-a][1,4]benzodiazepine;

9-bromo-1-[[(cyclopropylmethyl)ethylamino]methyl]-4-ethyl-6-(o-chlorophenyl)-4H-s-triazolo[4,3-a][1,4]benzodiazepine;

9-(trifluoromethyl)-1-[[(cyclopropylmethyl)propylamino]methyl]-6-(o-chlorophenyl)-4H-s-triazolo[4,3-a][1,4]benzodiazepine;

10-(trifluoromethyl)-1-[[(cyclopropylmethyl)ethylamino]methyl]-4-propyl-6-phenyl-4H-s-triazolo[4,3-a][1,4]benzodiazepine;

8-chloro-1-[[(cyclopropylmethyl)ethylamino]methyl]-4-methyl-6-phenyl-4H-s-triazolo[4,3-a][1,4]benzodiazepine;

7-bromo-1-[[(cyclopropylmethyl)propylamino]methyl]-6-(o-chlorophenyl)-4H-s-triazolo[4,3-a][1,4]benzodiazepine; 8-chloro-1-[(allylmethylamino)methyl]-6-(2,6-difluorophenyl)-4H-s-triazolo[4,3-a][1,4]benzodiazepine; 8-chloro-1-[(allylpropylamino)methyl]-4-methyl-6-(o-chlorophenyl)-4H-s-triazolo[4,3-a](allylethylamino)methyl]1,4]benzodiazepine; 8-nitro-1-[allylethylamino)methyl]-4-ethyl-6-phenyl-4H-s-triazolo[4,3-a][1,4]benzodiazepine; 8-bromo-1-[(allylpropylamino)methyl]-6-(2,6-difluorophenyl)-4H-s-triazolo[4,3-a][1,4]benzodiazepine; 7-(trifluoromethyl)-1-[(allylethylamino)methyl]-6-(o-chlorophenyl)-4H-s-triazolo[4,3-a][1,4]benzodiazepine; 9-bromo-1-[(allylmethylamino)methyl]-4-methyl-6-(o-chlorophenyl)-4H-s-triazolo[4,3-a][1,4]benzodiazepine; 8-chloro-1-[(allylethylamino)methyl]-4-ethyl-6-(m-fluorophenyl)-4H-s-triazolo[4,3-a][1,4]benzodiazepine; 8-fluoro-1-[(allylpropylamino)methyl]-6-(p-fluorophenyl)-4H-s-triazolo[4,3-a][1,4]benzodiazepine; 10-(trifluoromethyl)-1-[(allylethylamino)methyl]-4-propyl-6-phenyl-4H-s-triazolo[4,3-a][1,4]benzodiazepine; 8-chloro-1-[(dipropylamino)methyl]-6-(2,6-difluorophenyl)-4H-s-triazolo[4,3-a][1,4]benzodiazepine; 8-bromo-1-[(methylpropylamino)methyl]-4-methyl-6-phenyl-4H-s-triazolo[4,3-a][1,4]benzodiazepine; 8-(trifluoromethyl)-1-[(ethylpropylamino)methyl]-4-propyl-6-phenyl-4H-s-triazolo[4,3-a][1,4]benzodiazepine; 10-chloro-1-[(dimethylamino)methyl]-6-phenyl-4H-s-triazolo[4,3-a][1,4]benzodiazepine; 8-chloro-1-(piperidinomethyl)-4-ethyl-6-(2,6-difluorophenyl)-4H-s-triazolo[4,3-a][1,4]benzodiazepine; 7-chloro-1-(pyrrolidinomethyl)-4-methyl-6-(o-fluorophenyl)-4H-s-triazolo[4,3-a][1,4]benzodiazepine; and the like.

EXAMPLE 1

2',5-Dichloro-2-[3-(hydroxymethyl)-5-[(dimethylamino)methyl]-4H-1,2,4-triazol-4-yl]benzophenone A 3.5 g. (10.0 mmole) portion of 1-(hydroxymethyl)-6-(o-chlorophenyl)-8-chloro-4H-s-triazolo[4,3-a][1,4]benzodiazepine is treated with 13.1 g. (150 mmole) of an 88% formic acid solution and 6.75 ml. (90.0 mmole) of a 37% aqueous formaldehyde solution and heated to 100° C. for 3 hours. The reaction mixture is quenched in a cold 10% aqueous sodium hydroxide solution and extracted with chloroform. The chloroform extracts are washed with a saturated aqueous sodium chloride solution, dried over sodium sulfate and concentrated in vacuo to an oil which crystallizes from ethyl acetate/hexane mixtures to afford 800 mg. of 2',5-dichloro-2-[3-(hydroxymethyl)-5-[(dimethylamino)methyl]-4H-1,2,4-triazol-4-yl]benzophenone of melting point 138°–141° C. Anal. calcd. for $C_{19}H_{18}Cl_2N_4O_2$: C, 56.30; H, 4.48; N, 13.83; Cl, 17.49. Found: C, 56.26; H, 4.55; N, 13.75; Cl, 17.37.

EXAMPLE 2

2',5-Dichloro-2-[3,5-bis[(dimethylamino)methyl]-4H-1,2,4-triazol-4-yl]benzophenone A 3.86 g. (10.0 mmole) portion of 8-chloro-1-[(dimethylamino)methyl]-6-(o-chlorophenyl)-4H-s-triazolo-[4,3-a][1,4]benzodiazepine is treated with 13.1 g. (150 mmole) of an 88% formic acid solution, 6.75 ml. (90.0 mmole) of a 37% aqueous formaldehyde solution and heated to 100° C. for 3 hours to give 2',5-dichloro-2-[3,5-bis[(dimethylamino)methyl]-4H1,2,4-triazol-4-yl]benzophenone.

EXAMPLE 3

5-Chloro-2-[3,5-bis[(dimethylamino)methyl]-4H-1,2,4-triazol-4-yl]benzophenone

A solution of 650 mg. (1.8 mmole) of 8-chloro-1-[(dimethylamino)methyl]-6-phenyl-4H-s-triazolo[4,3-a][1,4]benzodiazepine is treated with 2.62 g. (30.0 mmole) of 88% formic acid solution, 1.22 ml. (16.2 mmole) of an aqueous formaldehyde solution and heated to 100° C. for 3 hours to give an oil which crystallizes from ethyl acetate giving 550 mg. (77%) of 5-chloro-2-[3,5-bis[(dimethylamino)methyl]-4H-1,2,4-triazol-4-yl]benzophenone of melting point 148°–152° C. The analytical sample has a melting point 150°–152° C. Anal. calcd. for $C_{21}H_{24}ClN_5O$: C, 63.39; H, 6.08; N, 17.60; Cl, 8.91. Found: C, 63.29; H, 6.15; H, 17.59; Cl, 8.91.

In an alternative manner, the products of example 1 can be obtained in the following manner:

EXAMPLE 2

2',5-Dichloro-2-[3-(hydroxymethyl)-5-[(dimethylamino)methyl]-4H-1,2,4-triazol-4-yl]benzophenone A 3.28 g. (10.0 mmole) portion of 8-chloro-6-(o-chlorophenyl)-4H-s-triazolo[4,3-][1,4]benzodiazepine is treated with 13.1 g. (150 mmole) of an 88% formic acid solution, 6.75 ml. (90.0 mmole) of a 37% aqueous formaldehyde solution and heated to 100° C. for 24 hours to give 2',5-dichloro-2-[3-(hydroxymethyl)-5-[(dimethylamino)methyl]-4H-1,2,4-triazol-4-yl]benzophenone of melting point 139°–141° C.

EXAMPLE 5

5-Chloro-2-[3-(hydroxymethyl)-5-[(dimethylamino)methyl]-4H-1,2,4-triazol-4-yl]benzophenone A stirred solution of 8-chloro-6-phenyl-4H-s-triazolo[4,3-a][1,4]benzodiazepine (1.18 g., 0.004 mole) in 88% formic acid (3.12 g., 0.06 mole) and 37% formaldehyde solution (2.92 g., 0.036 mole) is refluxed overnight under nitrogen. The reaction is cooled, quenched with cold 5% aqueous sodium hydroxide and extracted with chloroform. The extract is dried over anhydrous sodium sulfate, filtered through a celite (diatomaceous earth) pad and concentrated in vacuo. The oil is chromatographed on silica gel (100 g.) with 5% methanol-95% chloroform. The product thus obtained is crystallized from ethyl acetate-Skellysolve B hexanes to give 0.695 g. (47%) of 5-chloro-2-[3-(hydroxymethyl)-5-[(dimethylamino)methyl]-4H-1,2,4-triazol-4-yl]benzophenone of melting point 138°–141° C. The analytical sample has a melting point 139°–141° C. Anal. calcd for $C_{19}H_{19}ClN_4O_2$: C, 61.54; H, 5.16; Cl, 9.56; N, 15.11. Found: C, 61.70; H, 5.37; Cl, 9.63; N, 15.52.

EXAMPLE 6

5-Chloro-2',6'-difluoro-2-[3-(hydroxymethyl)-5-[(dimethylamino)methyl]-4H-1,2,4-triazol-4-yl]benzophenone In the manner given in Example 1, 8-chloro-1-(hydroxymethyl)-6-(2,6-difluorophenyl)-4H-s-triazolo[4,3-a][1,4]benzodiazepine is heated in formic acid with formalin to give 5-chloro-2',6'-difluoro-2-[3-(hydroxymethyl)-5-[(dimethylamino)methyl]-4H-1,2,4-triazol-4-yl]benzophenone. [(dimethylamino)-methyl]-4H-1,2,4-triazol-4-yl]benzophenone In the manner given in Example 1, 8-nitro-1-(hydroxymethyl)-6-(o-fluorophenyl)-4H-s-triazolo[4,3-a][1,4]benzodiazepine is heated in formic acid with aqueous formaldehyde to give 2'-fluoro-5-nitro-2-[3-(hydroxymethyl)-5-[(dimethylamino)methyl]-4H-1,2,4-triazol-4-yl]benzophenone.

EXAMPLE 8

2'-Chloro-5-(trifluoromethyl)-2-[3-(hydroxymethyl)-5-[(dimethylamino)methyl]-4H-1,2,4-triazol-4-yl]-benzophenone In the manner given in Example 1, 8-(trifluoromethyl)-1-(hydroxymethyl)-6-(o-chlorophenyl)-4H-s-triazolo[4,3-a][1,4]benzodiazepine is heated in formic acid with aqueous formaldehyde to give 2'-chloro-5-(trifluoromethyl)-2-[3-(hydroxymethyl)-5-[(dimethylamino)methyl]-4H-1,2,4-triazol-4yl]benzophenone.

EXAMPLE 9

2'-Chloro-2-[3-(hydroxymethyl)-5-[(dimethylamino)methyl]-4H-1,2,4-triazol-4-yl]benzophenone In the manner given in Example 1, 1-(hydroxymethyl-6-(o-chlorophenyl)-4H-s-triazolo[4,3-a][1,4]benzodiazepine is heated in formic acid with aqueous formaldehyde to give 2'-chloro-2-[3-(hydroxymethyl)-5-[(dimethylamino)methyl]-4H-1,2,4-triazol-4-yl]benzophenone.

EXAMPLE 10

2'-Chloro-5-fluoro-2-[3-(hydroxymethyl)-5-[(dimethylamino)methyl]-4H-1,2,4-triazol-4-yl]benzophenone In the manner given in Example 1, 8-fluoro-1-(hydroxymethyl)-6-(o-chlorophenyl)-4H-s-triazolo[4,3-a][1,4]benzodiazepine is heated in formic acid with aqueous formaldehyde to give 2'-chloro-5-fluoro-2-[3-(hydroxymethyl)-5-[(dimethylamino)methyl]-4H-1,2,4-triazol-4-yl]benzophenone.

EXAMPLE 11

5-Chloro-2-[3-[(diethylamino)methyl]-5-[(dimethylamino)methyl]-4H-1,2,4-triazol-4-yl]benzophenone In the manner given in Example 1, 8-chloro-1-[(diethylamino)methyl]-6-phenyl-4H-s-triazolo[4,3-a][1,4]benzodiazepine is heated in formic acid with aqueous formaldehyde to give 5-chloro-2-[3-[(diethylamino)methyl]-5-[(dimethylamino)methyl]-4H-1,2,4-triazol-4-yl]benzophenone.

EXAMPLE 12

5-Nitro-2-[3-[(diethylamino)methyl]-5-[(dimethylamino)methyl]-4H-1,2,4-triazol-4-yl]benzophenone In the manner given in Example 1, 8-nitro-1-[(diethylamino)methyl]-6-phenyl-4H-s-triazolo[4,3-a][1,4]-benzodiazepine is heated in formic acid with aqueous formaldehyde to give 5-nitro-2-[3-[(diethylamino)methyl]-5-[(dimethylamino)methyl]-4H-1,2,4-triazol-4-yl]benzophenone.

EXAMPLE 13

2'-Chloro-2-[3,5-bis[(dimethylamino)methyl]-4H-1,2,4-triazol-4-yl]benzophenone

In the manner given in Example 1, 1-[(dimethylamino)-methyl]-6-(o-chlorophenyl)-4H-s-triazolo[4,3-a][1,4]-benzodiazepine is heated in formic acid with aqueous formaldehyde to give 2'-chloro-2-[3,5-bis[(dimethylamino)-    -methyl]-4H-1,2,4-triazol-4-yl]benzophenone.

EXAMPLE 14

5-Chloro-2-[3-[[(2-propynyl)methylamino]-methyl]-5-[(dimethylamino)methyl]-4H-1,2,4-triazol-4-yl]-benzophenone In the manner given in Example 1, 8-chloro-1-[[(2-propynyl)amino]methyl]-6-phenyl-4H-s-triazolo[4,3-a][1,4-]benzodiazepine is heated in formic acid with aqueous formaldehyde to give 5-chloro-2-[3[(2-propynyl)methylamino]methyl]-5-[(dimethylamino)-methyl]-4H-1,2,4-triazol-4-yl]benzophenone.

EXAMPLE 15

2',5-Dichloro-2-[3-[[(2-propynyl)methylamino]methyl]-5-[(dimethylamino)methyl]-4H-1,2,4-triazol-4-yl]benzophenone In the manner given in Example 1, 8-chloro-1-[[(2-propynyl)amino]methyl]-6-(o-chlorophenyl)-4H-s-triazolo[4,3-a][1,4]benzodiazepine is heated in formic acid with aqueous formaldehyde to give 2',5-dichloro-2-[3-[[(2-propynyl)methylamino]methyl]-5-[(dimethylamino)methyl]-4H-1,2,4-triazol-4-yl]benzophenone.

EXAMPLE 16

2'-Chloro-5-fluoro-2-[3-[[(2propynyl)methylamino]methyl]-5-[(dimethylamino)methyl]-4H-1,2,4-triazol-4-yl]benzophenone In the manner given in Example 1,8-fluoro-1-[[(2-propynyl)amino]methyl]-6-(o-chlorophenyl)-4H-s-triazolo[4,3-a][1,4]benzodiazepine is heated in formic acid with aqueous formaldehyde to give 2'-chloro-5-fluoro-2-[3-[[(2-propynyl)methylamino]methyl]-5-[(dimethylamino)methyl]-4H-1,2,4-triazol-4-yl]benzophenone.

EXAMPLE 17

2'-Chloro-5-(trifluoromethyl)-2-[3-[[(2-propynyl)-methylamino]methyl]-5-[(dimethylamino)methyl]-4-H-1,2,4-triazol-4-yl]benzophenone In the manner given in Example 1,8-(trifluoromethyl)-1-[[(2-propynyl)amino]methyl]-6-(o-chlorophenyl)-4-H-s-triazolo[4,3-a][1,4]benzodiazepine is heated in formic acid with aqueous formaldehyde to give 2'-chloro-5-(trifluoromethyl)-2-[3-[[(2-propynyl)methylamino]-methyl]-5-[(dimethylamino)-methyl]-4H-1,2,4-triazol-4-yl]benzophenone.

EXAMPLE 18

5-Chloro-2',6'-difluoro-2-[3-[[(2-propynyl)-methylamino]methyl]-5-[(dimethylamino)methyl]-4H-1,2,4-triazol-4-yl]benzophenone In the manner given in Example 1, 8-chloro-1-[[(2propynyl)amino]methyl]-6-(2,6-difluorophenyl)-4H-s-triazolo[4,3-a][1,4]benzodiazepine is heated in formic acid with aqueous formaldehyde to give 5-chloro-2',6'-difluoro-2-[3-[[(2propynyl)methylamino]methyl]-5-(dimethylamino)methyl]-4H-1,2,4-triazol-4-yl]benzophenone.

EXAMPLE 19

2'-Chloro-5-nitro-2-[3-[[(2-propynyl)methylamino]methyl]-5-[(dimethylamino)methyl]-4H-1,2,4-triazol-4-yl]benzophenone In the manner given in Example 1, 8-nitro-1-[[(2-propynyl)amino]methyl]-6-(o-chlorophenyl)-4H-s-triazolo[4,3-a][1,4]benzodiazepine is heated in formic acid with aqueous formaldehyde to give 2'-chloro-5-nitro-2-[3-[[(2-propynyl)methylamino]methyl]-5-[(dimethylamino)methyl]-4H-1,2,4-triazol-4-yl]benzophenone.

EXAMPLE 20

5-Chloro-2-[3-[[(cyclopropylmethyl)methylamino]methyl]-5-[(dimethylamino)methyl]-4H-1,2,4-triazol-4-yl]benzophenone In the manner given in Example 1, 8-chloro-1-[[(cyclopropylmethyl)amino]methyl]-6-phenyl-4H-s-triazolo[4,3-a][1,4]benzodiazepine is heated in formic acid with aqueous formaldehyde to give 5-chloro-2-[3-[[(cyclopropylmethyl)methylamino]methyl]-5-[(dimethylamino)methyl]-4H-1,2,4-triazol-4-yl benzophenone.

EXAMPLE 21

5-Nitro-2-[3-[[(cyclopropylmethyl)methylamino]-methyl]-5-[(dimethylamino)methyl]-4H-1,2,4-triazol-4-yl]-benzophenone In the manner given in Example 1, 8-nitro-1-[[(cyclopropylmethyl)amino]methyl]-6-phenyl-4H-s-triazolo-[4,3-a][1,4]benzodiazepine is heated in formic acid with aqueous formaldehyde to give 5-nitro-2-[3-[[(cyclopropylmethyl)methylamino]methyl]-5-[(dimethylamino)methyl]-4H-1,2,4-triazol-4-yl]benzophenone.

EXAMPLE 22

2',5-Dichloro-2-[3-[[(cyclopropylmethyl)-methylamino]methyl-5-[(dimethylamino)methyl]-4H-1,2,4-triazol-4-yl]benzophenone In the manner given in Example 1, 8-chloro-1-[[(cyclopropylmethyl)amino]methyl]-6-(o-chlorophenyl)-4H-s-triazolo[4,3-a][1,4]benzodiazepine is heated in formic acid with aqueous formaldehyde to give 2',5-dichloro-2-[3-[[(cyclopropylmethyl)methylamino]methyl]-5-[(dimethylamino)methyl]-4H-1,2,4-triazol-4-yl]benzophenone.

EXAMPLE 23

5-Chloro-2-[3-[[(cyclopropylmethyl)methylamino]-methyl]-5-[(dimethylamino)methyl]-4H-1,2,4-triazol-4-yl]benzophenone In the manner given in Example 1, 8-chloro-1-[[(cyclopropylmethyl)methylamino]methyl]-6-phenyl-4H-s-triazolo[4,3-a][1,4]benzodiazepine is heated in formic acid with aqueous formaldehyde to give 5-chloro-2-[3-[[(cyclopropylmethyl)methylamino]methyl]-5-](dimethylamino)methyl]-4-H-1,2,4-triazol-4-yl]benzophenone. This product is identical to that given in Example 21.

EXAMPLE 24

5-Bromo-2-[3-[[(cyclopropylmethyl)ethylamino]-methyl]-5-[(dimethylamino)methyl]-4H-1,2,4-triazol-4-yl]benzophenone In the manner given in Example 1, 8-bromo-1-[[(cyclopropylmethyl)ethylamino]methyl]-6-phenyl-4H-s-triazolo[4,3-a][1,4]benzodiazepine is heated in formic acid with aqueous formaldehyde to give 5-bromo-2-[3-[[(cyclopropylmethyl)ethylamino]methyl]-5-[(dimethylamino)methyl]-4H-1,2,4-triazol-4-yl]benzophenone.

EXAMPLE 25

5-Chloro-2',6'-difluoro-2-[3-[[(cyclopropylmethyl)-propylamino]methyl]-5-[(dimethylamino)methyl]-4H-1,2,4-triazol-4-yl]benzophenone In the manner given in Example 1, 8-chloro-1[[(cyclopropylmethyl)propylamino]methyl]-6-(2,6-difluorophenyl)-4H-s-triazolo[4,3-a][1,4]benzodiazepine is heated with formic acid with aqueous formaldehyde to give 5-chloro-2',6'-difluoro-2-[3-[[(cyclopropylmethyl)propylamino]methyl]-5-[(dimethylamino)methyl]-4H-1,2,4-triazol-4-yl]benzophenone.

EXAMPLE 26

5-Nitro-2-[3-[[(cyclopropylmethyl)propylamino]-methyl]-5-[(dimethylamino)methyl]-4H-1,2,4-triazol-4-yl]benzophenone In the manner given in Example 1, 8-nitro-1-[[(cyclopropylmethyl)propylamino]methyl]-6-phenyl-4H-s-triazolo[4,3-a][1,4]benzodiazepine is heated in formic acid with aqueous formaldehyde to give 5-nitro-2-[3-[[(cyclopropylmethyl)propylamino]methyl]-5-[(dimethylamino)methyl]-4H-1,2,4-triazol-4-yl]benzophenone.

EXAMPLE 27

2',5-Difluoro-2-[3-[[(cyclopropylmethyl)ethylamino]methyl-5-[(dimethylamino)methyl]-4H-1,2,4-triazol-4-yl]benzophenone In the manner given in Example 1, 8-fluoro-1-[[(cyclopropylmethyl)ethylamino]methyl]-6-(ofluorophenyl)-4-H-s-triazolo[4,3a][1,4]benzodiazepine [[(cyclopropylmethyl)ethylamino]methyl]-6-(o-fluorophenyl)-4H-s-triazolo[4,3-a][1,4]benzodiazepine is heated in formic acid with aqueous formaldehyde to give 2',5-difluoro-2-[3-[[(cyclopropylmethyl)ethylamino]-methyl]-5-[(dimethylamino)methyl]-4H-1,2,4-triazol-4-yl]benzophenone.

EXAMPLE 28

4-(Trifluoromethyl)-2-[3-[[(cyclopropylmethyl)methylamino]methyl]-5-[(dimethylamino)methyl]-4H-1,2,4-triazol-4-yl]benzophenone In the manner given in Example 1, 9-(trifluoromethyl)-1-[[(cyclopropylmethyl)methylamino]methyl]-6-phenyl-4H-s-triazolo[4,3-a][1,4]benzodiazepine is heated in formic acid with aqueous formaldehyde to give 4-(trifluoromethyl)-2-[3-[[(cyclopropylmethyl)-methylamino]methyl]-5-[(dimethylamino)methyl]-4H-1,2,4-triazol-4-yl]benzophenone.

EXAMPLE 29

5-Chloro-2-[3-(allylmethylamino)methyl]-5-[(dimethylamino)methyl]-4H-1,2,4-triazol-4-yl]benzophenone In the manner given in Example 1, 8-chloro-1-[(allylamino)methyl]-6-phenyl-4H-s-triazolo[4,3-a][1,4]benzodiazepine is heated in formic acid with aqueous formaldehyde to give 5-chloro-2-[3-[(allylmethylamino)methyl]-5-[(dimethylamino)methyl]-4H-1,2,4-triazol-4-yl]benzophenone.

EXAMPLE 30

2',5-Dichloro-2-[3-[(allylmethylamino)methyl]-5-[(dimethylamino)methyl]-4H-1,2,4-triazol-4-yl]benzophenone In the manner given in Example 1, 8-chloro-1-[(allylamino)methyl]-6-(o-chlorophenyl)-4H-s-triazolo[4,3-a]-[1,4]benzodiazepine is heated in formic acid with aqueous formaldehyde to give 2',5-dichloro-2-[3-[(allylmethylamino)methyl]-5-[(dimethylamino)methyl]-4H-1,2,4-triazol-4-yl]benzophenone.

EXAMPLE 31

2',5-Dichloro-2-[3-[(allylmethylamino)methyl]-5-[(dimethylamino)methyl]-4H-1,2,4-triazol-4-yl]benzophenone In the manner given in Example 1, 8-chloro-1-[(allylmethylamino)methyl-6-(o-chlorophenyl)-4H-s-triazolo-[4,3-a][1,4]benzodiazepine is heated in formic acid with aqueous formaldehyde to give 2',5-dichloro-2-[3-[(allylmethylamino)methyl]-5-[(dimethylamino)methyl]-4H-1,2,4-triazol-4-yl]benzophenone. This compound is identical to that given in Example 32.

EXAMPLE 32

2'-Chloro-5-nitro-2-[3-[(allylmethylamino)-methyl]-5-[(dimethylamino)methyl]-4H-1,2,4-triazol-4-yl]-benzophenone In the manner given in Example 1, 8-nitro-1-[(allylmethylamino)methyl]-6-(o-chlorophenyl)-4H-s-triazolo-[4,3a][1,4-benzodiazepine is heated in formic acid with aqueous formaldehyde to give 2'-chloro-5-nitro-2-[3-[(allylmethylamino)methyl]-5-[(dimethylamino)methyl]-4H-1,2,4-triazol-4-yl]benzophenone.

EXAMPLE 33

5-Bromo-2-[3-[(allylethylamino)methyl]-5-[(dimethylamino)methyl]-4H-1,2,4-triazol-4-yl]benzophenone In the manner given in Example 1, 8-bromo-1-[(allylethylamino)methyl]-6-phenyl-4H-s-triazolo[4,3-a][1,4]benzodiazepine is heated in formic acid with aqueous formaldehyde to give 5-bromo-2-[3-[(allylethylamino)methyl]-5-[(dimethylamino)methyl]-4H-1,2,4-triazol-4-yl]benzophenone.

EXAMPLE 34

2'-Chloro-5-(trifluoromethyl)-2-[3-[(allylmethylamino)methyl]-5-[(dimethylamino)methyl]-4H-1,2,4-triazol-4-yl]benzophenone In the manner given in Example 1, 8-(trifluoromethyl)-1-[(allylmethylamino)methyl]-6-(o-chlorophenyl)-4H-s-triazolo[4,3-a][1,4]benzodiazepine is heated in formic acid with aqueous formaldehyde to give 2'-chloro-5-(trifluoromethyl)-2-[3-[(allylmethylamino)methyl]-5-[(dimethylamino)methyl]-4H-1,2,4-triazol-4-yl]benzophenone.

EXAMPLE 35

5-Chloro-2',6'-difluoro-2-[3-[(allylpropylamino)-methyl]-5-[(dimethylamino)methyl]-4H-1,2,4-triazol-4-yl]-benzophenone In the manner given in Example 1, 8-chloro-1-[(allylpropylamino)methyl]-6-(2,6-difluorophenyl)-4H-s-triazolo[4,3-a][1,4]benzodiazepine is heated in formic acid with aqueous formaldehyde to give 5-chloro-2',6'-difluoro-2-[3-[(allylpropylamino)methyl]-5-[(dimethylamino)methyl]-4H-1,2,4-triazol-4-yl]benzophenone.

EXAMPLE 36

5-Nitro-2- 3-[(allylpropylamino)methyl]-5-[(dimethylamino)methyl]-4H-1,2,4-triazol-4-yl]benzophenone In the manner given in Example 1, 8-nitro-1-[(allylpropylamino)methyl]-6-phenyl-4H-s-triazolo[4,3-a][1,4]benzodiazepine is heated in formic acid with aqueous formaldehyde to give 5-nitro-2-[3-[(allylpropylamino)methyl]-5-[(dimethylamino)methyl]-4H-1,2,4triazol-4-yl]-benzophenone.

EXAMPLE 37

2',5-difluoro-2-[3-[(allylethylamino)methyl]-5-[(dimethylamino)methyl]-4-H-1,2,4-triazol-4-yl]benzophenone In the manner given in Example 1, 8-fluoro-1-[(allylethylamino)methyl]-6-(o-fluorophenyl)-4H-s-triazolo[4,3-a][1,4]benzodiazepine is heated in formic acid with aqueous formaldehyde to give 2',5-difluoro-2-[3-[(allylethylamino)methyl]-5-[(dimethylamino)-methyl]-4H-1,2,4-triazol-4-yl]benzophenone.

EXAMPLE 38

4-(Trifluoromethyl)-2-[3-[(allylmethylamino)methyl]-5-[(dimethylamino)methyl]-4H-1,2,4-triazol-4-yl]-benzophenone In the manner given in Example 1, 9-(trifluoromethyl)-1-[(allylmethylamino)methyl-6-phenyl-4H-s-triazolo[4,3-a]-[1,4]-benzodiazepine is heated in formic acid with aqueous formaldehyde to give 4-(trifluoromethyl)-2-[3-[(allylmethylamino)methyl]-5-[(dimethylamino)methyl]-4H-1,2,4-triazol-4-yl]benzophenone.

EXAMPLE 39

5-Chloro-2-[3-(pyrrolidino)methyl]-5-[(dimethylamino)methyl]-4H-1,2,4-triazol-4-yl]benzophenone In the manner given in Example 1, 8-chloro-1-(pyrrolidinomethyl)-6-phenyl-4H-s-triazolo[4,3-a][1,4]benzodiazepine is heated in formic acid with aqueous formaldehyde to give 5-chloro-2-[3-(pyrrolidinomethyl)-5-[(dimethylamino)-methyl]-4H-1,2,4-triazol-4yl]benzophenone.

EXAMPLE 40

2',5-Dichloro-2-[3-(pyrrolidinomethyl)-5-[(dimethylamino)methyl]-4H-1,2,4-triazol-4-yl]benzophenone In the manner given in Example 1, 8-chloro-1-(pyrrolidinomethyl)-6-(o-chlorophenyl)-4H-s-triazolo[4,3-a][1,4]-benzodiazepine is heated in formic acid with aqueous formaldehyde to give 2',5'-dichloro-2-[3-(pyrrolidinomethyl)-5-[(dimethylamino)methyl]-4H-1,2,4-triazol-4-yl]-benzophenone.

EXAMPLE 41

5-(Trifluoromethyl2-[3-(pyrrolidinomethyl)-5-[(dimethylamino)methyl]-4H-1,2,4-triazol-4-yl]benzophenone In the manner given in Example 1, 8-(trifluoromethyl)-1-(pyrrolidinomethyl)-6-phenyl-4H-s-triazolo[4,3-a][1,4]benzodiazepine is heated in formic acid with aqueous formaldehyde to give 5-(trifluoromethyl)-2-[3-(pyrrolidinomethyl)-5-[(dimethylamino)methyl]-4H-1,2,4-triazol-4-yl]-benzophenone.

EXAMPLE 42

5-Chloro-2-[3-(piperidinomethyl)-5-[(dimethylamino)methyl]-4H-1,2,4-triazol-4-yl]benzophenone In the manner given in Example 1, 8-chloro-1-(piperidinomethyl)-6-phenyl-4H-s-triazolo[4,3-a][1,4]benzodiazepine is heated in formic acid with aqueous formaldehyde to give 5-chloro-2-[3-(piperidinomethyl)-5-[(dimethylamino)methyl]-4H-1,2,4-triazol -4-yl]benzophenone.

EXAMPLE 43

5-Fluoro-2-[3-(piperidinomethyl)-5-[(dimethylamino)methyl]-4H-1,2,4-triazol-4-yl]benzophenone In the manner given in Example 1, 8-fluoro-1-(piperidinomethyl)-6-phenyl-4H-s-triazolo[4,3-a][1,4]benzodiazepine is heated in formic acid with aqueous formaldehyde to give 5-fluoro-2-[3-(piperidinomethyl)-5-[(dimethylamino)methyl]-4H-1,2,4-triazol-4-yl]benzophenone.

EXAMPLE 44

2',5-Dichloro-2-[3-(morpholinomethyl)-5-[(dimethylamino)methyl]-4H-1,2,4-triazol-4-yl]benzophenone In the manner given in Example 1, 8-chloro-1-(morpholinomethyl)-6-(o-chlorophenyl)-4H-s-triazolo[[4,3-a][1,4]benzodiazepine is heated in formic acid with aqueous formaldehyde to give 2',5-dichloro-2-[3-(morpholinomethyl)-5-[(dimethylamino)methyl]-4H-1,2,4-triazol-4-yl]-benzophenone.

EXAMPLE 45

5-Nitro-2-[3-(morpholinomethyl)-5-[(dimethylamino)methyl]-4H-1,2,4-triazol-4-yl]benzophenone In the manner given in Example 1, 8-nitro-1-(morpholinomethyl)-6-phenyl-4H-s-triazolo[4,3-a][1,4]-benzodiazepine is heated in formic acid with aqueous formaldehyde to give 5-nitro-2-[3-(morpholinomethyl)-5-[(dimethylamino)methyl]-4H-1,2,4-triazol-4-yl]benzophenone.

EXAMPLE 46

5-Bromo-2'-chloro-2-[3-(morpholinomethyl)-5-[(dimethylamino)methyl]-4H-1,2,4-triazol-4-yl benzophenone In the manner given in Example 1, 8-bromo-1-(morpholinomethyl)-6-(o-chlorophenyl)-4H-s-triazolo[4,3-a][1,4]benzodiazepine is heated in formic acid with aqueous formaldehyde to give 5-bromo-2'-chloro-2-[3-(morpholinonomethyl)-5-[(dimethylamino)methyl]-4H-1,2,4-triazol-4-yl]benzophenone.

In the manner given in the previous examples, other compounds of formula IA can be prepared. Such compounds comprise:

5-bromo-2-[3-(hydroxymethyl)-5-[(dimethylamino)methyl]-4H-1,2,4-triazol-4-yl]benzophenone;

5-chloro-2',6'-difluoro-2-[3-(hydroxymethyl)-5-[(dimethylamino)methyl]-4H-1,2,4-triazol-4-yl]benzophenone;

5-chloro-2-[3-(hydroxymethyl)-5-[1-(dimethylamino)ethyl]-4H-1,2,4-triazol-4-yl]benzophenone;

4-bromo-2-[3-(hydroxymethyl)-5-[1-(dimethylamino)butyl-4H-1,2,4-triazol-4-yl]benzophenone;

2'-chloro-5-nitro-2-[3-(hydroxymethyl)-5-[1-(dimethylamino)propyl]-4H-1,2,4-triazol-4-yl]benzophenone;

5-chloro-2-[3-[[(2-propynyl)ethylamino]methyl]-5-[(dimethylamino)methyl]-4H-1,2,4-triazol-4-yl]benzophenone;

5-fluoro-2-[3-[[(2-propynyl)propylamino]methyl]-5-[(dimethylamino)methyl]-4H-1,2,4-triazol-4-yl]benzophenone;

5-bromo-2-[3-[[(2-propynyl)ethylamino]methyl]-5-[(dimethylamino)methyl]-4H-1,2,4-triazol-4-yl]benzophenone;

5-chloro-2',6'-difluoro-2-[3-[[(2-propynyl)propylamino]methyl]-5-[(dimethylamino)methyl]-4H-1,2,4-triazol-4-yl]-benzophenone;

5-(trifluoromethyl)-2-[3-]](2-propynyl)methylamino]methyl]-5-[1-(dimethylamino)butyl]-4H-1,2,4-triazol-4-yl]benzopheone;

4-nitro-2-[3-[[(2-propynyl)ethylamino]methyl]-5-[1-(dimethylamino)ethyl]-4H-1,2,4-triazol-4-yl]benzophenone;

3',5'-dichloro-2-[3-[[(2-propynyl)methylamino]methyl]-5-[1-(dimethylamino)propyl]-4H-1,2,4-triazol-4-yl]benzophenone;

4'-chloro-6-(trifluoromethyl)-2-[3-[[(2-propynyl)propylamino]methyl]-5-[1-(dimethylamino)ethyl]-4-H-1,2,4-triazol-4-yl]benzophenone;

2'-chloro-5-nitro-2-[3-[[(cyclopropylmethyl)ethylamino]methyl]-5-[(dimethylamino)methyl]-4H-1,2,4-triazol-4-yl]benzophenone;

2',5-dichloro-2-[3-[[(cyclopropylmethyl)methylamino]-methyl]-5-[1-(dimethylamino)ethyl]-4H-1,2,4-triazol-4-yl]benzophenone;

3',4-dichloro-2-[3-[[(cyclopropylmethyl)ethylamino]methyl]-5-[1-(dimethylamino)propyl]-4H-1,2,4-triazol-4-yl]benzophenone;

4-bromo-2'-chloro-2-[3-[[(cyclopropylmethyl)propylamino]methyl]-5-[(dimethylamino)methyl]-4H-1,2,4-triazol-4-yl]benzophenone;

6-chloro-2'-fluoro-2-[3-[[(cyclopropylmethyl)propylamino]methyl]-5-[(dimethylamino)methyl]-4H-1,2,4-triazol-4-yl]benzophenone;

2'-chloro-3-(trifluoromethyl)-2-[3-[[(cyclopropylmethyl)methylamino]methyl]-5-[(dimethylamino)methyl]-4-H-1,2,4-triazol-4-yl]benzophenone;

2',4-dichloro-2-[3-[[(cyclopropylmethyl)methylamino]-methyl]-5-[(dimethylamino)methyl]-4H-1,2,4-triazol-4-yl]benzophenone;

4-bromo-2'-chloro-2-[3-[[(cyclopropylmethyl)ethylamino]-methyl]-5-[1-(dimethylamino)propyl]-4H-1,2,4-triazol-4-yl]benzophenone;

2'-chloro-4-(trifluoromethyl)-2-[3-[[(cyclopropylmethyl)-propylamino]methyl]-5-[(dimethylamino)methyl]-4H-1,2,4-triazol-4-yl]benzophenone;

3-(trifluoromethyl)-2-[3-[[(cyclopropylmethyl)ethylamino]-methyl]-5-[1-(dimethylamino)butyl]-4H-1,2,4-triazol-4-yl]benzophenone;

5-chloro-2-[3-[[(cyclopropylmethyl)ethylamino]-methyl]-5-[1-(dimethylamino)ethyl]-4H-1,2,4-triazol-4-yl]benzophenone;

6-bromo-2'-chloro-2-[3-[[(cyclopropylmethyl)propylamino]-methyl]-5-[(dimethylamino)methyl]-4-H-1,2,4-triazol-4-yl]benzophenone;

5-chloro-2',6'-difluoro-2-[3-[(allylmethylamino)methyl]-5-[(dimethylamino)methyl]-4H-1,2,4-triazol-4-yl]benzophenone;

2',5-dichloro-2-[3-[(allylpropylamino)methyl]-5-[1-(dimethylamino)ethyl]-4H-1,2,4-triazol-4-yl]benzophenone;

5-nitro-2-[3-[(allylethylamino)methyl]-5-[1-(dimethylamino)propyl]-4H-1,2,4-triazol-4-yl]benzophenone;

5-bromo-2',6'-difluoro-2-[3-[(allylpropylamino)methyl]-5-[(dimethylamino)methyl]-4H-1,2,4-triazol-4-yl]benzophenone;

2'-chloro-6-(trifluoromethyl)-2-[3-[(allylethylamino)-methyl]-5-[(dimethylamino)methyl]-4H-1,2,4-triazol-4-yl]-benzophenone;

4-bromo-2'-chloro-2-[3-[(allylmethylamino)methyl]-5-[1-(dimethylamino)ethyl]-4H-1,2,4-triazol-4-yl]benzophenone;

5-chloro-3'-fluoro-2-[3-[(allylethylamino)methyl]-5-[1-(dimethylamino)propyl]-4H-1,2,4-triazol-4-yl]benzophenone;

4,4'-difluoro-2-[3-[(allylpropylamino)methyl]-5-[(dimethylamino)methyl]-4H-1,2,4-triazol-4-yl]benzophenone;

3-(trifluoromethyl)-2-[3-[(allylethylamino)methyl]-5-[1-(dimethylamino)butyl]-4H-1,2,4-triazol-4-yl]benzophenone;

5-chloro-2',6'-difluoro-2-[3-[(dipropylamino)methyl]-5-[(dimethylamino)methyl]-4H-1,2,4-triazol-4-yl]benzophenone;

5-bromo-2-[3-[(methylpropylamino)methyl]-5-[1-(dimethylamino)ethyl]-4H-1,2,4-triazol-4-yl]benzophenone;

5-(trifluoromethyl)-2-[(ethylpropylamino)methyl]-5-[1-(dimethylamino)butyl]-4H-1,2,4-triazol-4-yl]benzophenone;

3-chloro-2-[3,5-bis](dimethylamino)methyl]-4H-1,2,4-triazol-4-yl]benzophenone; and the like.

EXAMPLE 47

5-Chloro-2-[3-[(allylamino)methyl]-5-[(dimethylamino)methyl]-4H-1,2,4-triazol-4-yl]benzophenone A solution of 1.01 g. (3.00 mmole) of 5-chloro-2-[3-(hydroxymethyl)-5-[(dimethylamino)methyl]-4H-1,2,4-triazol-4-yl]benzophenone in 15 ml. of methylene chloride and cooled to 0° C. is treated dropwise with 0.378 g. (3.30 mmole) of methane sulfonylchloride. The mixture is stirred for ½ hour, poured onto ice, and extracted with a saturated aqueous sodium bicarbonate solution. The organic layer is removed, dried with anhydrous sodium sulfate and concentrated in vacuo to an oil. This resulting oil, dissolved in 20 ml. of tetrahydrofuran, is treated with 0.56 g. (10 mmole) of allylamine and 0.996 g. (6.0 mmole) of potassium iodide and heated to reflux for 24 hours. The reaction mixture is poured onto a cold (0°–5° C.) 10% aqueous sodium hydroxide solution and extracted with chloroform. The chloroform extract is dried with anhydrous sodium sulfate and concentrated in vacuo to give 5-chloro-2-[3-[(allylamino)methyl]-5-[(dimethylamino)methyl]-4H-1,2,4-triazol-4-yl]benzophenone.

EXAMPLE 48

2',5-Dichloro-2-[3-[(allylamino)methyl]-5-[(dimethylamino)methyl]-4H-1,2,4-triazol-4-yl]benzophenone In the manner given in Example 47, 2',5-dichloro-2-[3-(hydroxymethyl)-5-[(dimethylamino)methyl]-4H-1,2,4-triazol-4-yl]benzophenone is treated first with methanesulfonic anhydride followed by allylamine to give 2',5-dichloro-2-[3-[(allylamino)methyl]-5-[(dimethylamino)methyl]-4H-1,2,4-triazol-4-yl]benzophenone.

EXAMPLE 49

2'-Chloro-2-[3-[(allylamino)methyl]-5-[(dimethylamino)methyl]-4H-1,2,4-triazol-4-yl]benzophenone In the manner given in Example 47, 2'-chloro-2-[3-(hydroxymethyl)-5-[(dimethylamino)methyl]-4H-1,2,4-triazol-4-yl]benzophenone is treated first with methanesulfonyl chloride followed by allylamine to give 2'-chloro-2-[3-[(allylamino)methyl]-5-[(dimethylamino)methyl]-4H-1,2,4-triazol-4-yl]benzophenone.

EXAMPLE 50

5-Chloro-2-[3-[[(cyclopropylmethyl)amino]-methyl]-5-[(dimethylamino)methyl]-4H-1,2,4-triazol-4-yl]-benzophenone In the manner given in Example 47, 5-chloro-2-[3-(hydroxymethyl)-5-[(dimethylamino)methyl]-4H-1,2,4-triazol-4- yl]benzophenone is treated first with methanesulfonyl chloride followed by (cyclopropylmethyl)amine to give 5-chloro-2-[3-[[(cyclopropylmethyl)amino]methyl]-5-[(dimethylamino)methyl]-4H-1,2,4-triazol-4-yl]benzophenone.

EXAMPLE 51

2',5-Dichloro-2-[3-[[(cyclopropylmethyl)amino]-methyl]-5-[(dimethylamino)methyl]-4H-1,2,4-triazol-4-yl]benzophenone In the manner given in Example 47, 2',5-dichloro-2-[3-(hydroxymethyl)-5-[(dimethylamino)methyl]-4H-1,2,4-triazol-4-yl]benzophenone is treated first with ethanesulfonyl chloride followed by (cyclopropylmethyl)amine, to give 2',5-dichloro-2-[3-[[(cyclopropylmethyl)amino]methyl]-5-[(dimethylamino)-methyl]-4H-1,2,4-triazol-4-yl]benzophenone.

EXAMPLE 52

5-Chloro-2',6'-difluoro-2-[3-[[(2-propynyl)-amino]-methyl]-5-[(dimethylamino)methyl]-4H-1,2,4-triazol-4-yl]benzophenone In the manner given in Example 47, 5-chloro-2',6'-difluoro-2-[3-(hydroxymethyl)-5-[(dimethylamino)-methyl]-4H-1,2,4-triazol-4-yl]benzophenone is treated first with p-toluenesulfonyl chloride followed by propargylamine, to give 5-chloro-2',6'-difluoro-2-[3-[[(2-propynyl)amino]methyl]-5-[(dimethylamino)methyl]-4H-1,2,4-triazol-4-yl]benzophenone.

EXAMPLE 53

5-Chloro-2-[3-[[(2-propynyl)amino]methyl-5-[(dimethylamino)methyl]-4H-1,2,4-triazol-4-yl]benzophenone In the manner given in Example 47, 5-chloro-2-[3-(hydroxymethyl)-5-[(dimethylamino)methyl]-4H-1,2,4-triazol-4-yl]benzophenone is treated first with methanesulfonyl chloride followed by propargylamine to give 5-chloro-2-[3-[[(2-propynyl)amino]methyl]-5-[(dimethylamino)methyl]-4H-1,2,4-triazol-4-yl]benzophenone.

EXAMPLE 54

5-(Trifluoromethyl)-2-[3-[(allylamino)methyl]-5-[(dimethylamino)methyl]-4H-1,2,4-triazol-4-yl]benzophenone In the manner given in Example 47, 5-(trifluoromethyl)-2-[3-(hydroxymethyl)-5-](dimethylamino)methyl]-4H-1,2,4-triazol-4-yl]benzophenone is treated first with methanesulfonic anhydride followed by allylamine to give 5-(trifluoromethyl)-2-[3-[(allylamino)-methyl]-5-[(dimethylamino)methyl-4H-1,2,4-triazol-4-yl]benzophenone.

EXAMPLE 55

2'-Chloro-5-nitro-2-[3-[[(2-propynyl)amino]-methyl]-5-[(dimethylamino)methyl]-4H-1,2,4-triazol-4-yl]benzophenone In the manner given in Example 47, 2'-chloro-5-nitro-2-[3-(hydroxymethyl)-5-[(dimethylamino)methyl]-4H-1,2,4-triazol-4-yl]benzophenone is treated first with methanesulfonyl chloride followed by propargylamine, to give 2'-chloro-5-nitro-2-[3-[[(2-propynyl)amino]methyl]-5-[(dimethylamino)methyl]-4H-1,2,4-triazol-4-yl]benzophenone.

EXAMPLE 56

5-Bromo-2-[3-[[(cyclopropylmethyl)amino]- methyl]-5-[(dimethylamino)methyl]-4H-1,2,4-triazol-4-yl]-benzophenone In the manner given in Example 47, 5-bromo-2-[3-(hydroxymethyl)-5-[(dimethylamino)methyl]-4H-1,2,4-triazol-4-yl]benzophenone is treated first with methanesulfonyl chloride followed by (cyclopropylmethyl)-amine to give 5-bromo-2-[3-[[(cyclopropylmethyl)amino]-methyl]-5-[(dimethylamino)methyl]-4H-1,2,4-triazol-4-yl]-benzophenone.

In the manner given in Examples 47 through 56 other compounds of formula IB can be prepared. Representative compounds thus include:

2',5-dichloro-2-[3-[[(2-propynyl)amino]methyl]-5-[(dimethylamino)methyl]-4H-1,2,4-triazol-4-yl]benzophenone;

5-nitro-2-[3-[[(cyclopropylmethyl)amino]methyl]-5-[(dimethylamino)methyl)-4H-1,2,4-triazol-4-yl]benzophenone;

5-chloro-2-[3-[(allylamino)methyl]-5-[1-(dimethylamino)ethyl]-4H-1,2,4-triazol-4-yl]benzophenone;

5-bromo-2'-chloro-2-[3-[[(cyclopropylmethyl)amino]-methyl]-5-[1-(dimethylamino)butyl]-4H-1,2,4-triazol-4-yl]benzophenone;

5-(trifluoromethyl)2-[3-[[(2-propynyl)amino]methyl]-5-[1-(dimethylamino)propyl]-4H-1,2,4-triazol-4-yl]benzophenone;

4-chloro-2-[3-[(allylamino)methyl]-5-[1-(dimethylamino)ethyl]-4H-1,2,4-triazol-4-yl]benzophenone;

6-bromo-2'-chloro-2-[3-[[(cyclopropylmethyl)amino]-methyl]-5-[(dimethylamino)methyl]-4H-1,2,4-triazol-4-yl]-benzophenone; and the like.

Treating the compounds of formula I with pharmacologically acceptable acid such as hydrochloric, hydrobromic, phosphoric, sulfuric, acetic, propionic, toluenesulfonic, methanesulfonic, tartaric, citric, lactic, malic, maleic, cyclohexanesulfamic acids produces the pharmacologically acceptable salts of these compounds of formula I which can be used like the free base compounds of formula I. Salt formation is achieved in conventional manner by reacting the compounds of formula I with excess of a selected acid in a suitable medium e.g. water, a lower alkanol, ether, or acetone and recovering the salt by evaporating the solvent, preferably in vacuo.

I claim:

1. A compound of the formula I:

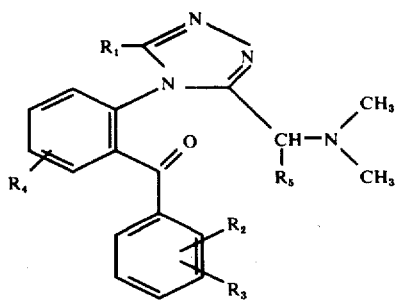

wherein R₁ is hydroxymethyl or -CH₂NR₆R₇, in which R₆ is —CH₂—C≡CH, —CH₂—CH=CH₂,

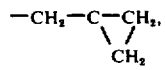

or alkyl of 1 to 3 carbon atoms inclusive, R₇ is hydrogen or alkyl of 1 to 3 carbon atoms, or together

is pyrrolidino, piperidino, or morpholino, wherein R₂ is hydrogen, chlorine or fluorine; wherein R₃ is hydrogen or fluorine if R₂ is fluorine; wherein R₄ is fluorine, chlorine, bromine, nitro, or trifluoromethyl; and wherein R₅ is hydrogen, methyl or ethyl, and the pharmacologically acceptable acid addition salts thereof.

2. A compound of the formula IC:

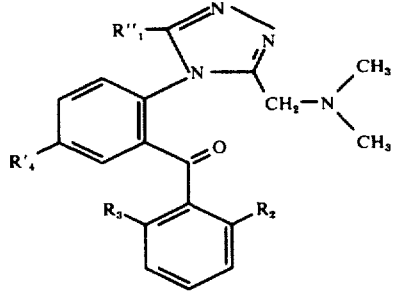

wherein R''₁ is hydroxymethyl or (dimethylamino)methyl; R₂ and R'₄ are hydrogen, chlorine, or fluorine; R₃ is hydrogen or fluorine if R₂ is fluorine; and the pharmacologically acceptable acid addition salts thereof.

3. A compound of the formula ID:

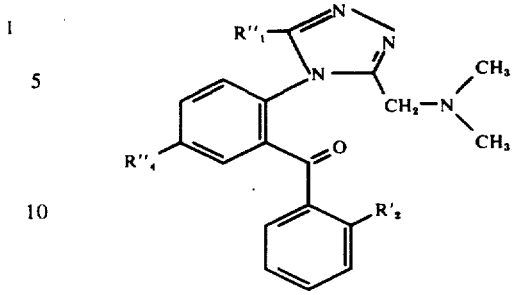

wherein R''₁ is hydroxymethyl or (dimethylamino)methyl; and wherein R'₂ and R''₄ are hydrogen or chlorine, and the pharmacologically acceptable acid addition salts thereof.

4. A compound of the formula:

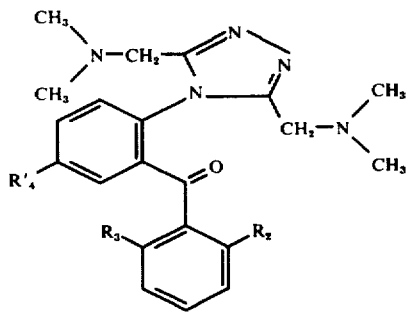

wherein R₂ and R'₄ are hydrogen, chlorine, or fluorine; R₃ is hydrogen or fluorine and the pharmacologically acceptable acid addition salts thereof.

5. A compound of the formula

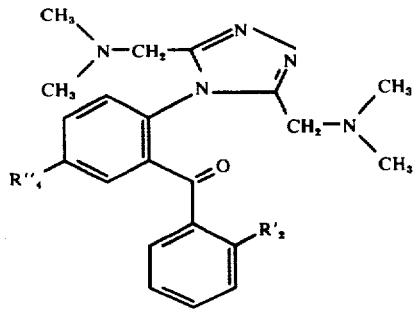

wherein R'₂ and R''₄ are hydrogen or chlorine and the pharmacologically acceptable acid addition salts thereof.

6. A compound according to claim 1, wherein R₁ is [(2-propynyl)methylamino]methyl, R₂ and R₃ are hydrogen and R₄ is 5-chloro and the compound is therefore 5-chloro-2-[3-[[(2-propynyl)methylamino]methyl]-5-[(dimethylamino)methyl]-4H-1,2,4-triazol-4-yl]benzophenone.

7. A compound according to claim 3, wherein R'₁ is hydroxymethyl, R'₂ is chloro, R''₄ is hydrogen and the compound is therefore 2'-chloro-2-[3-(hydroxymethyl)-5-[(dimethylamino)methyl]-4H-1,2,4-triazol-4-yl]benzophenone.

8. A compound according to claim 3, wherein R'₁ is hydroxymethyl, R'₂ is hydrogen, R''₄ is chloro and the compound is therefore 5-chloro-2-[3-(hydroxymethyl)-5-[(dimethylamino)methyl]-4H-1,2,4-triazol-4-yl]benzophenone.

9. A compound according to claim 3 wherein R''₁ is hydroxymethyl, R'₂ and R''₄ are chloro and the compound is therefore 2',5-dichloro-2-[3-(hydroxymethyl)-5-[(dimethylamino)methyl]-4H-1,2,4-triazol-4-yl]benzophenone.

10. A compound according to claim 5, wherein R'₁ is (dimethylamino)methyl, R'₂ is chloro, R''₄ is hydrogen, and the compound is therefore 2'-chloro-2-[3,5-bis-[(dimethylamino)methyl]-4H-1,2,4-triazol-4-yl]benzophenone.

11. A compound according to claim 5, wherein R'₁ is (dimethylamino)methyl, R'₂ is hydrogen, R''₄ is chloro and the compound is therefore 5-chloro-2-[3,5-bis]-(dimethylamino)methyl]-4H-1,2,4-triazol-4-yl]benzophenone.

12. A compound according to claim 5, wherein R'₁ is (dimethylamino)methyl, R'₂ and R''₄ are chloro and the compound is therefore 2',5-dichloro-2-[3,5-bis[-(dimethylamino)methyl]-4H-1,2,4-triazol-4-yl]benzophenone.

13. A process for the production of a compound of the formula IA:

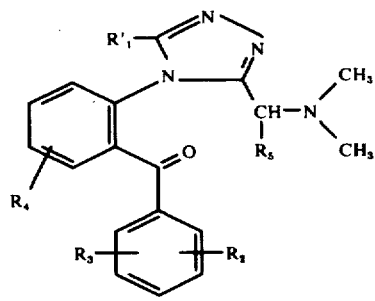

wherein R'₁ is hydroxymethyl or -CH₂NR₆R'₇, in which R₆ is —CH₂—CH≡CH, —CH₂—CH=CH₂,

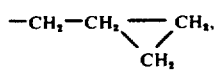

or alkyl of 1 to 3 carbon atoms inclusive, R'₇ is alkyl of 1 to 3 carbon atoms, inclusive, or together

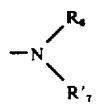

is pyrrolidino, piperidino, or morpholino; wherein R₂ is hydrogen, chlorine, or fluorine; wherein R₃ is hydrogen or fluorine with the proviso that if R₂ is chloro, R₃ is not fluoro; wherein R₄ is hydrogen, fluorine, chlorine, bromine, nitro, or trifluoromethyl; and wherein R₅ is hydrogen, methyl or ethyl, are produced by heating a compound of the formula II:

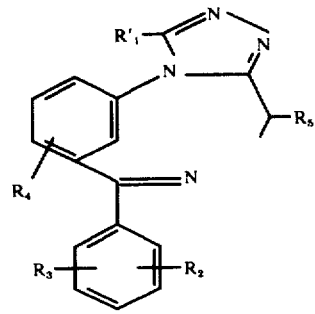

wherein R'₁, R₂, R₃, R₄, and R₅ are defined as herein above, with formaldehyde in formic acid to obtain a compound of formula IA above.

14. A process for the production of a compound of the formula IB:

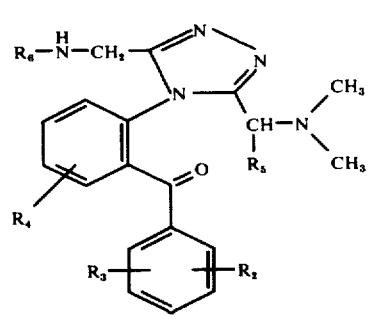

wherein R₂ is hydrogen, chlorine, or fluorine; R₃ is hydrogen or fluorine with the proviso that if R₂ is chloro, R₃ is not fluoro; wherein R₄ is hydrogen, fluorine, chlorine, bromine, nitro, or trifluoromethyl; and wherein R₅ is hydrogen, methyl, or ethyl; R₆ is -CH₂-C≡CH, —CH₂—CH=CH₂,

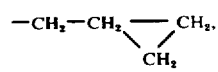

or alkyl of 1 to 3 carbon atoms inclusive, which comprises: 1. heating a compound of the formula IIA

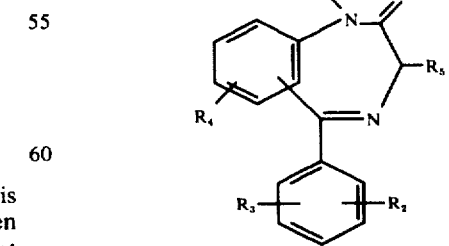

wherein R₂, R₃, R₄, and R₅ are defined as herein above, with formaldehyde in formic acid to obtain a compound of the formula III:

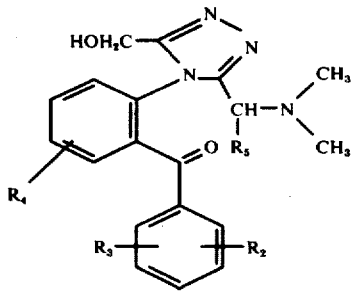

wherein $R_2$, $R_3$, $R_4$, and $R_5$ are defined as herein above;

2. treating III with a compound of the formula

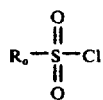

or of the formula

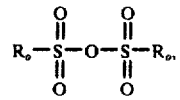

wherein $R_0$ is alkyl of from 1 to 3 carbon atoms inclusive, phenyl or p-tolyl, to obtain a compound of formula IV:

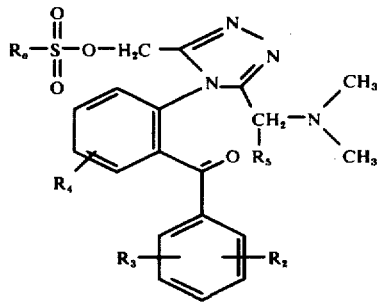

wherein $R_0$, $R_2$, $R_3$, $R_4$, and $R_5$ are defined as above;

4. treating compound IV with a primary amine of the formula $R_6NH_2$ to obtain a compound of formula IB wherein $R_2$, $R_3$, $R_4$, $R_5$, and $R_6$ are defined as above.

* * * * *